United States Patent
Tochio et al.

(10) Patent No.: US 9,963,691 B2
(45) Date of Patent: May 8, 2018

(54) β-FRUCTOFURANOSIDASE

(71) Applicants: B FOOD SCIENCE CO., LTD., Chita-shi (JP); MICROBIOPHARM JAPAN CO., LTD., Chuo-ku (JP)

(72) Inventors: Takumi Tochio, Chita (JP); Saki Nakamura, Chita (JP); Misa Yahara, Chita (JP); Tadashi Fujii, Chuo-ku (JP); Keisuke Tamura, Chuo-ku (JP)

(73) Assignees: B FOOD SCIENCE CO., LTD., Aichi (JP); MICROBIOPHARM JAPAN CO., LTD., Tokyo (JP)

( * ) Notice: Subject to any disclaimer, the term of this patent is extended or adjusted under 35 U.S.C. 154(b) by 0 days. days.

(21) Appl. No.: 15/107,500

(22) PCT Filed: Dec. 26, 2014

(86) PCT No.: PCT/JP2014/084680
§ 371 (c)(1),
(2) Date: Jun. 23, 2016

(87) PCT Pub. No.: WO2015/099166
PCT Pub. Date: Jul. 2, 2015

(65) Prior Publication Data
US 2016/0319263 A1    Nov. 3, 2016

(30) Foreign Application Priority Data

Dec. 27, 2013  (JP) .................. 2013-273402

(51) Int. Cl.
*C12N 9/26*     (2006.01)
*C12P 19/14*    (2006.01)

(52) U.S. Cl.
CPC ............ *C12N 9/2431* (2013.01); *C12P 19/14* (2013.01); *C12Y 302/01026* (2013.01)

(58) Field of Classification Search
None
See application file for complete search history.

(56) References Cited

U.S. PATENT DOCUMENTS 6,337,201 B1    1/2002 Yana et al.

FOREIGN PATENT DOCUMENTS

| EP | 0 889 134 A1 | 1/1999 |
| EP | 1 726 655 A1 | 11/2006 |

(Continued)

OTHER PUBLICATIONS

PIR Accession No. A25040, published Jul. 9, 2004.*

(Continued)

*Primary Examiner* — Richard C Ekstrom
(74) *Attorney, Agent, or Firm* — RatnerPrestia

(57) ABSTRACT

An improved β-fructofuranosidase is provided. The improved β-fructofuranosidase may comprise an amino acid sequence having 60% or higher identity to the amino acid sequence of SEQ ID NO: 2, and may contain an amino acid mutation that replaces histidine (H) corresponding to position 395 counted from the N terminus of SEQ ID NO: 2 with arginine (R) or lysine (K), an amino acid mutation that replaces leucine (L) at position 123 counted from the N terminus of SEQ ID NO: 2 with cysteine (C), and/or an amino acid mutation that replaces phenylalanine (F) at position 473 counted from the N terminus of SEQ ID NO: 2 with tyrosine (Y).

18 Claims, 1 Drawing Sheet

(56) References Cited

FOREIGN PATENT DOCUMENTS

| EP | 1 878 738 A1 | 1/2008 |
|---|---|---|
| JP | 3628336 B2 | 3/2005 |
| JP | 4162147 B2 | 10/2008 |

OTHER PUBLICATIONS

GenPept, Accession code ACB95643 (Jul. 16, 2012).
GenPept, Accession code ACC75109 (Jul. 14, 2012).
GenPept, Accession code Q43998 (Oct. 19, 2013).
GenPept, Accession code YP_110564 (Jul. 22, 2013).
GenPept, Accession code ZP_00218900 (Oct. 4, 2004).
Homann et al., Biochm. J., 407:189-98 (2007).
Japanese Office Action for Japanese Patent Application No. 2015-540936 dated Oct. 21, 2015 (with English Translation).
Japanese Office Action for Japanese Patent Application No. 2015-540936 dated Mar. 30, 2016 (with English Translation).
Martinez-Fleites et al., Biochem. J., 390:19-27 (2005).
PCT/JP2014/084680 International Search Report issued by Japanese Patent Office dated Feb. 3, 2015.
Tambara et al., Biotechnol. Lett., 21:117-21 (1999).
Visnapuu et al., J. Biotechnol., 155:338-49 (2011).
Yanase et al., J. Biochem., 132:565-72 (2002).
Chambert et al., Biochem. J., 279:35-41 (1991).
Goldman et al., J. of Biological Chemistry, 283(47):32209-217 (2008).
Levansucrase [*Pseudomonas syringae* pv. Tomato str. DC3000], GenPept, Accession Code AAO59056.1 (Jul. 20, 2012).
Li et al., Acta Biochimica Polonica, 55(1):201-6 (2008).
Nakamura et al., "Engineering of beta-fructofuranosidase from Beljerinckia indica for effective synthesis of Kestose", Abstracts of the Annual Meeting of the Society for Biotechnology, 66:212, 3P-073 (2014).
Tamas et al., J. Bacteriol, 192(17):4532-33 (2010).
Yanase, J. Appl. Glycosci., 44(2):203-11 (1997) with English Abstract.
Yanase et al., J. Biochem., 132(4):565-72 (2002).
Daude et al., Natural Product Reports, 29(9):945-60 (2012).
Extended European Search Report for Japanese Application No. PCT/JP2014/084680 by Daniel Pilate dated Jun. 28, 2017.
Jung et al., Nature Biotechnology, 16(6):576-50 (1998).

\* cited by examiner

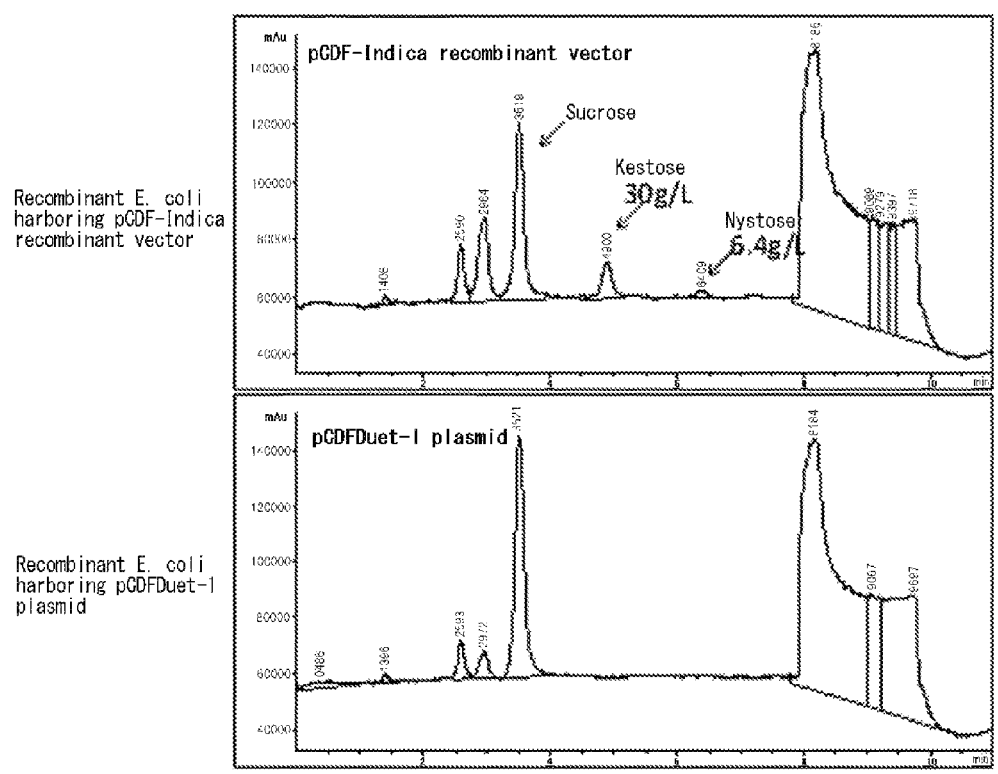

β-FRUCTOFURANOSIDASE

CROSS-REFERENCE TO RELATED APPLICATIONS

This application is a U.S. National Phase Application of PCT International Application PCT/JP2014/084680, filed Dec. 26, 2014 which claims priority to Japanese Application No. 2013-273402, filed Dec. 27, 2013, the contents of which are incorporated herein by reference in their entireties for all purposes.

TECHNICAL FIELD

The present invention relates to an improved β-fructofuranosidase and particularly relates to an improved β-fructofuranosidase that can efficiently form kestose in a large amount while effectively suppressing the formation of by-products such as nystose, a polypeptide comprising an amino acid sequence thereof, a DNA encoding the improved β-fructofuranosidase, a recombinant vector comprising the DNA, a transformant obtained by transferring the DNA or the recombinant vector to a host, a method for producing an improved β-fructofuranosidase, and a method for producing kestose using the same.

BACKGROUND OF THE INVENTION

β-fructofuranosidases are enzymes that recognize fructose in sucrose and have the activity of hydrolyzing the sucrose into fructose and glucose (sucrose hydrolysis activity). Some β-fructofuranosidases have the activity of transferring the fructose formed by hydrolysis to sucrose (fructose transfer activity) and form a trisaccharide kestose in which one molecule of glucose is bonded to two molecules of fructose.

Among such kestoses, 1-kestose retains sweetness similar to sucrose (sugar) and is known as a useful oligosaccharide, for example, because this saccharide has approximately half of the calorie of sugar while offering approximately ⅓ of the sweetness of sugar, rarely increases blood glucose levels when ingested, and exhibits antiallergic functions (Patent Literature 1). For example, a β fructofuranosidase derived from *Aspergillus niger* and a β fructofuranosidase variant containing an amino acid mutation in the amino acid sequence thereof are disclosed (Patent Literature 2) as β-fructofuranosidases that form 1-kestose.

CITATION LIST

Patent Literature

Patent Literature 1: Japanese Patent No. 4162147
Patent Literature 2: Japanese Patent No. 3628336

SUMMARY OF THE INVENTION

Technical Problem

In kestose production using a β-fructofuranosidase, a tetrasaccharide nystose is usually formed as a by-product. Nystose is difficult to separate from kestose by chromatography and thus tends to remain in a reaction solution even after chromatographic separation and purification steps. In addition, the nystose that exists in more than a certain amount in the solution inhibits kestose crystallization in a crystallization step. From these facts, the efficient production of kestose requires reducing the formation of the nystose. Accordingly, there has been a demand for a β-fructofuranosidase that can efficiently form kestose with a small rate of formation of by-products such as nystose.

The present invention has been made in order to solve such problems, and an object of the present invention is to provide an improved β-fructofuranosidase that can efficiently form kestose in a large amount while reducing the rate of formation of by-products such as nystose, a polypeptide comprising an amino acid sequence thereof, a DNA encoding the improved β fructofuranosidase, a recombinant vector comprising the DNA, a transformant obtained by transferring the DNA or the recombinant vector to a host, a method for producing an improved β-fructofuranosidase, and a method for producing kestose using the same.

Solution to Problem

The present inventors have conducted diligent studies and consequently found that an amino acid mutation that replaces histidine (H) corresponding to position 395 counted from the N terminus of an amino acid sequence of wild-type β-fructofuranosidase represented by SEQ ID NO: 2 in alignment with arginine (R) or lysine (K) is introduced to an amino acid sequence of a β-fructofuranosidase having 60% or higher identity to the amino acid sequence (SEQ ID NO: 2) of wild-type β-fructofuranosidase derived from *Beijerinckia indica* subsp. *indica* NBRC3744 (hereinafter, abbreviated to "*B. Indica*"), whereby the resulting β-fructofuranosidase remarkably reduces the rate of formation of by-products such as nystose, increases the rate of formation of kestose, and increases the amount of kestose formed.

The present inventors have also found that at least one amino acid mutation selected from amino acid mutations i) to iii): i) an amino acid mutation that replaces leucine (L) at position 123 counted from the N terminus with cysteine (C), ii) an amino acid mutation that replaces histidine (H) at position 395 counted from the N terminus with arginine (R) or lysine (K), and iii) an amino acid mutation that replaces phenylalanine (F) at position 473 counted from the N terminus with tyrosine (Y) is introduced to the amino acid sequence of wild-type β-fructofuranosidase represented by SEQ ID NO: 2, whereby the resulting β-fructofuranosidase remarkably reduces the rate of formation of by-products such as nystose, increases the rate of formation of kestose, and increases the amount of kestose formed.

The present inventors have also found that at least one amino acid mutation selected from amino acid mutations i) and iii): i) an amino acid mutation that replaces leucine (L) at position 123 counted from the N terminus with cysteine (C) and iii) an amino acid mutation that replaces phenylalanine (F) at position 473 counted from the N terminus with tyrosine (Y) is introduced to the amino acid sequence of wild-type β-fructofuranosidase represented by SEQ ID NO: 2, whereby the resulting β-fructofuranosidase remarkably increases the rate of formation of lactosucrose and the amount of lactosucrose formed.

Thus, the following inventions have been completed on the basis of these findings:

(1) An improved β-fructofuranosidase according to one embodiment of the present invention comprises an amino acid sequence having 60% or higher identity to an amino acid sequence of wild-type β-fructofuranosidase represented by SEQ ID NO: 2 and the amino acid sequence of the improved β-fructofuranosidase contains an amino acid mutation that replaces histidine (H) corresponding to position 395 counted from the N terminus of the amino acid sequence of wild-type β fructofuranosidase represented by SEQ ID NO: 2 in alignment with arginine (R) or lysine (K).

(2) An improved β fructofuranosidase according to another embodiment of the present invention comprises the following amino acid sequence (a) or (b): (a) an amino acid sequence derived from an amino acid sequence of wild-type β-fructofuranosidase represented by SEQ ID NO: 2 by the introduction of one or two or more amino acid mutations selected from the following i) to iii): i) an amino acid mutation that replaces leucine (L) at position 123 counted from the N terminus with cysteine (C), ii) an amino acid mutation that replaces histidine (H) at position 395 counted from the N terminus with arginine (R) or lysine (K), and iii) an amino acid mutation that replaces phenylalanine (F) at position 473 counted from the N terminus with tyrosine (Y); and (b) an amino acid sequence derived from the amino acid sequence (a) by the deletion, substitution, insertion, or addition of one or several amino acids except for the mutated amino acid, and having β-fructofuranosidase activity.

(3) A polypeptide according to the present invention comprises an amino acid sequence of the improved β-fructofuranosidase according to (1) or (2).

(4) A DNA according to the present invention encodes the improved β-fructofuranosidase according to (1) or (2).

(5) A recombinant vector according to the present invention comprises the DNA according to (4).

(6) A transformant according to the present invention is a transformant obtained by transferring the DNA according to (4) or the recombinant vector according to (5) to a host.

(7) For the transformant according to the present invention, the host to which the DNA according to (4) or the recombinant vector according to (5) is transferred may be *E. coli*.

(8) A method for producing an improved β-fructofuranosidase according to the present invention comprises a step of obtaining an improved β-fructofuranosidase from cultures obtained by culturing the transformant according to (6) or (7).

(9) A method for producing kestose according to the present invention comprises a step of contacting sucrose with the improved β-fructofuranosidase according to (1) or (2), the transformant according to (6) or (7), or cultures obtained by culturing the transformant according to (6) or (7).

Advantageous Effects of Invention

The improved β-fructofuranosidase, the transformant and the method for producing kestose according to the present invention allow kestose to be efficiently produced in a large amount while reducing the rate of formation of by-products such as nystose. Furthermore, the polypeptide, the DNA, the recombinant vector, the transformant and the method for producing an improved β-fructofuranosidase according to the present invention can yield an improved β-fructofuranosidase that can efficiently produce kestose in a large amount while reducing the rate of formation of nystose.

BRIEF DESCRIPTION OF THE DRAWINGS

FIG. 1 shows HPLC chromatograms showing the proportion of each saccharide contained in reaction solutions for kestose formation reaction using recombinant *E. coli* harboring a pCDF-*Indica* recombinant vector (upper diagram) or a pCDFDuet-1 plasmid (lower diagram).

DETAILED DESCRIPTION OF THE INVENTION

Hereinafter, the improved β-fructofuranosidase, the polypeptide, the DNA, the recombinant vector, the transformant, the method for producing an improved β-fructofuranosidase, and the method for producing kestose according to the present invention will be described in detail.

Kestose is usually formed by the bonding of fructose to sucrose and can include 3 types: 1-kestose, 6-kestose, and neokestose, depending on the fructose-binding position. Specifically, 1-kestose is formed by the bonding of fructose to a fructose unit in sucrose through a β(2→1) bond; 6-kestose is formed by the bonding of fructose to a fructose unit in sucrose through a β(2→6) bond; and neokestose is formed by the bonding of fructose to a glucose unit in sucrose through a β(2→6) bond. Nystose is a tetrasaccharide that is formed by the bonding of fructose to a fructose unit in 1-kestose through a β(2→1) bond.

In the present invention, the "kestose" means a trisaccharide in which one molecule of glucose is bonded to two molecules of fructose, and encompasses 1-kestose, 6-kestose, and neokestose.

Lactosucrose is a trisaccharide in which fructose, glucose, and galactose are bonded, and is chemically represented by β-D-fructofuranosyl-4-O-β-D-galactopyranosyl-α-D-glucopyranoside or 4G-galactosyl sucrose. Specifically, this saccharide is characterized by having substructures of sucrose and lactose in its molecular structure and also called "lactose oligosaccharide" or "lactose fructose oligosaccharide". The lactosucrose is known as a useful oligosaccharide, for example, because of improving feces or bowel movement by increasing bifidobacteria in the intestine.

The lactosucrose is formed by allowing a β-fructofuranosidase to act on a carbohydrate containing a terminal fructose residue, such as sucrose, and lactose to bond the fructose to the lactose. In this context, specific examples of the "carbohydrate containing a terminal fructose residue" can include: disaccharides containing a terminal fructose residue, such as sucrose; oligosaccharides containing a terminal fructose residue, such as kestose; polysaccharides containing a terminal fructose residue; sugar alcohols containing a terminal fructose residue; and glycosides containing a terminal fructose residue.

In the present invention, the "β-fructofuranosidase" may be used interchangeably with "fructosyltransferase", "saccharase", "β-D-fructofuranosidase", "invertase", or "invertin". In the present invention, the "wild-type β-fructofuranosidase" refers to a β-fructofuranosidase consisting of an amino acid sequence lacking an amino acid mutation introduced by use of a genetic engineering approach. The "improved β-fructofuranosidase" refers to a β-fructofuranosidase comprising an amino acid sequence derived from the amino acid sequence of wild-type β-fructofuranosidase by the introduction of one or two or more amino acid mutations.

The improved β-fructofuranosidase according to one embodiment of the present invention comprises an amino acid sequence having 60% or higher identity to the amino acid sequence of wild-type β fructofuranosidase represented by SEQ ID NO: 2 wherein the amino acid sequence of the improved β fructofuranosidase contains an amino acid mutation that replaces histidine (H) corresponding to position 395 counted from the N terminus of the amino acid sequence of wild-type β-fructofuranosidase represented by SEQ ID NO: 2 in alignment with arginine (R) or lysine (K).

The identity between the amino acid sequence of wild-type β-fructofuranosidase represented by SEQ ID NO: 2 and the other amino acid sequence(s) can be confirmed according to a routine method and can be confirmed, for example, using a program such as FASTA (http://www.genome.JP/tools/fasta/), Basic local alignment search tool (BLAST; http://www.ncbi.nlm.nih.gov.), or Position-Specific Iterated BLAST (PSI-BLAST; http://www.ncbi.nlm.nih.gov.). In this context, the "identity" refers to the degree of exact match.

The amino acid sequence of the β-fructofuranosidase comprising an amino acid sequence having 60% or higher identity to the amino acid sequence of wild-type β-fructofuranosidase represented by SEQ ID NO: 2 can be obtained by deleting, substituting, inserting, or adding one or several amino acids in the amino acid sequence of SEQ ID NO: 2 such that the identity to the amino acid sequence of SEQ ID NO: 2 does not fall within a range lower than 60%. Also, this amino acid sequence of the β-fructofuranosidase can be obtained by homology search for the amino acid sequence of SEQ ID NO: 2 according to a routine method from an amino acid sequence database such as Protein Information Resource (PIR), SWISS-PROT, TrEMBL, Protein Research Foundation (PRF), or GenPept (NCBI Protein database) using a program such as FASTA (http://www.genome.JP/tools/fasta/), Basic local alignment search tool (BLAST; http://www.ncbi.nlm.nih.gov.), or Position-Specific Iterated BLAST (PSI-BLAST; http://www.ncbi.nlm.nih.gov.).

The amino acid sequence of the β-fructofuranosidase comprising an amino acid sequence having 60% or higher identity to the amino acid sequence of wild-type β-fructofuranosidase represented by SEQ ID NO: 2 may be an amino acid sequence of a β-fructofuranosidase derived from any organism including bacteria, yeasts, molds, and plants. Specific examples of the amino acid sequence of the β-fructofuranosidase comprising an amino acid sequence having 60% or higher identity to the amino acid sequence of wild-type β-fructofuranosidase represented by SEQ ID NO: 2 can include an amino acid sequence derived from the amino acid sequence of SEQ ID NO: 2 by the deletion, substitution, insertion, or addition of one or several amino acids such that the identity to the amino acid sequence of SEQ ID NO: 2 (hereinafter, also referred to as "predetermined identity") does not fall within a range lower than 60%, an amino acid sequence of a β-fructofuranosidase derived from *Beijerinckia indica* subsp. *indica* ATCC9039 (GenBank: ACB95643.1; predetermined identity: 99%), an amino acid sequence of a β-fructofuranosidase derived from *Burkholderia cenocepacia* (GenBank: CCE47348.1; predetermined identity: 77%), an amino acid sequence of a β-fructofuranosidase derived from *Burkholderia phymatum* STM815 (GenBank: ACC75109.1; predetermined identity: 75%), an amino acid sequence of a β-fructofuranosidase derived from *Burkholderia vietnamiensis* (GenBank: ERJ38440.1; predetermined identity: 77%), an amino acid sequence of a β fructofuranosidase derived from *Burkholderia ambifaria* AMMD (GenBank: ACB66635.1; predetermined identity: 76%), an amino acid sequence of a β fructofuranosidase derived from *Burkholderia cepacia* GG4 (GenBank: AFQ50734.1; predetermined identity: 76%), an amino acid sequence of a β-fructofuranosidase derived from *Burkholderia graminis* (GenBank: EDT09014.1; predetermined identity: 74%), an amino acid sequence of a β-fructofuranosidase derived from *Cupriavidus* sp. HPC(L) (GenBank: ESJ23133.1; predetermined identity: 70%), an amino acid sequence of a β-fructofuranosidase derived from *Burkholderia pseudomallei* 1106a (GenBank: AFR18711.1; predetermined identity: 73%), and an amino acid sequence of a β-fructofuranosidase derived from *Gluconacetobacter diazotrophicus* SRT4 (GenBank: AAB36606.1; predetermined identity: 66%).

In this context, in the present invention, examples of the number of amino acids to be deleted, substituted, inserted, or added in the phrase "amino acid sequence derived from the amino acid sequence of SEQ ID NO: 2 by the deletion, substitution, insertion, or addition of one or several amino acids such that the identity to the amino acid sequence of SEQ ID NO: 2 does not fall within a range lower than 60%" can include 1 to 200, 1 to 180, 1 to 160, 1 to 140, 1 to 120, 1 to 100, and 1 to 80, preferably 1 to 60, more preferably 1 to 50, further preferably 1 to 40, still further preferably 1 to 30.

Examples of the identity value for the "amino acid sequence having identity to the amino acid sequence of wild-type β-fructofuranosidase represented by SEQ ID NO: 2" according to the present invention can include 60% or higher and can further include 65% or higher, 70% or higher, 75% or higher, 80% or higher, 85% or higher, 90% or higher, and 95% or higher. Examples of the identity value to an "amino acid sequence (which corresponds to positions 29 to 534 of SEQ ID NO: 2) except for a signal sequence (which corresponds to positions 1 to 28 of SEQ ID NO: 2) in the amino acid sequence of wild-type β-fructofuranosidase represented by SEQ ID NO: 2" can include 65% or higher, 66% or higher, 70% or higher, 75% or higher, 80% or higher, 85% or higher, 90% or higher, and 95% or higher.

The alignment is also called "sequence alignment" and has the same meaning as this term. In the present invention, the alignment can be performed according to a routine method and can be performed, for example, using a program such as FASTA (http://www.genome.JP/tools/fasta/), Basic local alignment search tool (BLAST; http://www.ncbi.nlm.nih.gov.), Position-Specific Iterated BLAST (PSI-BLAST; http://www.ncbi.nlm.nih.gov.), CLUSTALW (http://www.genome.jp/ja/), or MAFFT (http://www.genome.jp/ja/).

Next, the improved β-fructofuranosidase according to another embodiment of the present invention comprises the following amino acid sequence (a) or (b):
(a) an amino acid sequence derived from the amino acid sequence of wild-type β-fructofuranosidase represented by SEQ ID NO: 2 by the introduction of one or two or more amino acid mutations selected from the following i) to iii):
  i) an amino acid mutation that replaces leucine (L) at position 123 counted from the N terminus with cysteine (C),
  ii) an amino acid mutation that replaces histidine (H) at position 395 counted from the N terminus with arginine (R) or lysine (K), and
  iii) an amino acid mutation that replaces phenylalanine (F) at position 473 counted from the N terminus with tyrosine (Y); and
(b) an amino acid sequence derived from the amino acid sequence (a) by the deletion, substitution, insertion, or addition of one or several amino acids except for the mutated amino acid, and having β-fructofuranosidase activity.

The "amino acid sequence derived by the deletion, substitution, insertion, or addition of one or several amino acids" in (b) means an amino acid sequence obtained by the deletion, substitution, insertion, or addition of any number of amino acids selected from, for example, 1 to 30 or 1 to 20, preferably 1 to 15, more preferably 1 to 10, further preferably 1 to 5 amino acids.

A feature of all of these improved β-fructofuranosidases according to the present invention is to increase the amount of kestose formed and remarkably reduce the rate of formation of by-products such as nystose, as compared with the wild-type β-fructofuranosidase.

When the improved β-fructofuranosidase according to the present invention comprises the following amino acid sequence (c) or (d), a feature of this improved β-fructofuranosidase is to increase the rate of formation of lactosucrose and the amount of lactosucrose formed, as compared with the wild-type β-fructofuranosidase:

(c) an amino acid sequence derived from the amino acid sequence of wild-type β fructofuranosidase represented by SEQ ID NO: 2 by the introduction of one or two amino acid mutations selected from the following i) and iii):

i) an amino acid mutation that replaces leucine (L) at position 123 counted from the N terminus with cysteine (C), and iii) an amino acid mutation that replaces phenylalanine (F) at position 473 counted from the N terminus with tyrosine (Y); and (d) an amino acid sequence derived from the amino acid sequence (c) by the deletion, substitution, insertion, or addition of one or several amino acids except for the mutated amino acid, and having β-fructofuranosidase activity.

The improved β-fructofuranosidase according to the present invention can be obtained according to a routine method. Examples of such a method can include a chemical synthesis method, and a method based on a gene recombination technique. In the chemical synthesis method, for example, the improved β-fructofuranosidase according to the present invention can be synthesized according to a chemical synthesis technique such as Fmoc method (fluorenylmethyloxycarbonyl method) or tBoc method (t-butyloxycarbonyl method) on the basis of amino acid sequence information on the improved β-fructofuranosidase according to the present invention. Alternatively, the improved β-fructofuranosidase according to the present invention may be synthesized using any of various commercially available peptide synthesizers.

In the method based on a gene recombination technique, the improved β-fructofuranosidase according to the present invention can be expressed in a suitable expression system to obtain the improved β-fructofuranosidase according to the present invention. Specifically, a DNA encoding the improved β fructofuranosidase according to the present invention is transferred to an appropriate host to obtain a transformant. Alternatively, as shown in Examples 3 and 4 mentioned later, a DNA encoding the improved β fructofuranosidase according to the present invention is inserted to an appropriate vector to obtain a recombinant vector. Then, the recombinant vector is transferred to an appropriate host to obtain a transformant. Then, the obtained transformant can be cultured and allowed to express an improved β-fructofuranosidase to obtain the improved β-fructofuranosidase according to the present invention.

In this context, the DNA encoding the improved β-fructofuranosidase according to the present invention can be synthesized using any of various commercially available DNA synthesizers and can also be obtained by polymerase chain reaction (PCR) with a DNA encoding wild-type β-fructofuranosidase or a DNA encoding a improved β-fructofuranosidase as a template.

In the case of obtaining, for example, a DNA encoding the improved β-fructofuranosidase comprising an amino acid sequence containing an amino acid mutation, as shown in Examples 3 and 4 mentioned later, a DNA primer encoding the amino acid mutation to be introduced is first designed. The DNA primer can be used in PCR with a DNA encoding wild-type β-fructofuranosidase or an improved β-fructofuranosidase lacking the amino acid mutation as a template to obtain the DNA of interest.

A DNA encoding the improved β-fructofuranosidase comprising the amino acid sequence (b) can also be obtained by PCR. Specifically, a DNA primer encoding an amino acid sequence corresponding to the amino acid deletion, substitution, insertion, or addition site in the amino acid sequence (a) is first designed. The DNA primer can be used in PCR with a DNA encoding the amino acid sequence (a) as a template to obtain the DNA of interest.

In the present invention, whether or not a protein has β-fructofuranosidase activity can be confirmed according to a routine method. For example, as shown in Examples 2(1) [1-3], 2(2) [2-1]<2-1-3>, and 3(1) [1-3] mentioned later, the protein is incubated in a reaction solution containing sucrose, or a transformant allowed to express the protein is cultured in a reaction solution containing sucrose. Then, the kestose content of the reaction solution is measured by high-performance liquid chromatography (HPLC) or the like. As a result, the protein can be determined as having β-fructofuranosidase activity when the kestose content is significantly large.

The present invention also provides a polypeptide comprising an amino acid sequence of the improved β-fructofuranosidase. The description about the same or equivalent constitution of the polypeptide according to the present invention as in the aforementioned improved β-fructofuranosidase according to the present invention will be omitted here.

The polypeptide according to the present invention is not particularly limited by its sequence length as long as the polypeptide comprises the amino acid sequence of the improved β-fructofuranosidase according to the present invention. The polypeptide according to the present invention may consist only of the amino acid sequence of the improved β-fructofuranosidase according to the present invention or may consist of an amino acid sequence derived from the amino acid sequence of the improved β fructofuranosidase according to the present invention by the addition of one or several amino acid residues to the amino terminus and/or the carboxyl terminus thereof. The polypeptide according to the present invention can be obtained in the same way as the aforementioned method for obtaining the improved β-fructofuranosidase according to the present invention.

The present invention further provides a DNA encoding the improved β-fructofuranosidase. The description about the same or equivalent constitution of the DNA encoding the improved β-fructofuranosidase according to the present invention as in the aforementioned improved β-fructofuranosidase and polypeptide according to the present invention will be omitted here.

The present invention further provides a recombinant vector comprising the DNA encoding the improved β-fructofuranosidase. The description about the same or equivalent constitution of the recombinant vector according to the present invention as in the aforementioned improved β-fructofuranosidase, polypeptide, and DNA according to the present invention will be omitted here.

The recombinant vector according to the present invention can be obtained, for example, by inserting the DNA encoding the improved β-fructofuranosidase according to the present invention to a vector. The insertion of the DNA to a vector can be performed according to a routine method and can be performed, for example, by ligating the DNA with a DNA fragment of a linearized vector. In this context, examples of the vector can include phage vectors, plasmid vectors, cosmids, and phagemids. The vector can be appropriately selected according to a host, ease of operation, etc. The recombinant vector according to the present invention may contain a selective marker gene for a transformant (e.g., a drug resistance gene and an auxotrophic marker gene), a promoter and a transcriptional or translational control signal (e.g., a transcription initiation signal, a ribosomal binding site, a translation termination signal, and a transcription termination signal) necessary for the expression of the improved β-fructofuranosidase, and the like, in addition to the DNA encoding the improved β-fructofuranosidase according to the present invention.

The present invention also provides a transformant. The description about the same or equivalent constitution of the transformant according to the present invention as in the aforementioned improved β-fructofuranosidase, polypeptide, DNA, and recombinant vector according to the present invention will be omitted here.

The transformant according to the present invention is obtained by transferring the DNA encoding the improved β-fructofuranosidase or the recombinant vector comprising the DNA encoding the improved β-fructofuranosidase according to the present invention to a host. In this context, examples of the host can include bacteria such as *E. coli* and *Bacillus subtilis*, yeasts, molds, and filamentous fungi. The host can be appropriately selected according to the type of the recombinant vector, ease of operation, etc. The transfer of the DNA or the recombinant vector to a host (transformation) can be performed according to a routine method. For example, the transfer of the recombinant vector using a plasmid to *E. coli* can be performed by adding the recombinant vector to competent cells of *E. coli*, leaving the resulting cells standing on ice for 30 minutes, subsequently placing the cells in a water bath of 42° C., leaving the cells standing for 45 seconds, then leaving the cells standing on ice for 2 minutes, and then adding a medium thereto, followed by shaking at 37° C. for 1 hour. Also, a homologous recombination method can be used for directly transferring the DNA of interest to the chromosome of the host.

The present invention further provides a method for producing an improved β-fructofuranosidase. The method for producing an improved β-fructofuranosidase according to the present invention comprises a step of obtaining an improved β-fructofuranosidase from cultures obtained by culturing the transformant according to the present invention. The description about the same or equivalent constitution of the method for producing an improved β-fructofuranosidase according to the present invention as in the aforementioned improved β-fructofuranosidase, polypeptide, DNA, recombinant vector, and transformant according to the present invention will be omitted here.

In the step of obtaining the improved β-fructofuranosidase from cultures obtained by culturing the transformant according to the present invention, the method for obtaining the improved β-fructofuranosidase can be appropriately selected according to the form of the transformant, etc. Specifically, the cultures obtained by culturing the transformant may be directly obtained as the improved β-fructofuranosidase, or the improved β-fructofuranosidase may be obtained by purification from the cultures.

Examples of the method for directly obtaining the cultures obtained by culturing the transformant as the improved β-fructofuranosidase when the DNA or the recombinant vector is designed such that the improved β fructofuranosidase is expressed on cell surface or intracellularly by the transformant can include a method which involves centrifuging the cultures to recover the transformant, which is then obtained directly as the improved β-fructofuranosidase, and a method which involves homogenizing the recovered transformant to obtain the homogenate as the improved β-fructofuranosidase.

Examples of the method for purifying the improved β-fructofuranosidase from the cultures when the DNA or the recombinant vector is designed such that the improved β-fructofuranosidase is secreted into the outside of the transformant can include a method which involves recovering a culture supernatant by the centrifugation of the cultures to purify the improved β-fructofuranosidase. When the improved β-fructofuranosidase is expressed in the inside of the transformant, the improved β-fructofuranosidase can be purified by recovering the transformant precipitated by the centrifugation of the cultures, suspending the recovered transformant in a buffer solution, homogenizing the transformant by, for example, freezing-thawing, ultrasonication, or grinding, and then recovering a supernatant by the centrifugation of the homogenate. Other examples of the purification method can include a method which involves subjecting the cultures to heat treatment, salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, isoelectric focusing electrophoresis, or the like.

The present invention further provides a method for producing kestose. The method for producing kestose according to the present invention comprises a step of contacting sucrose with the improved β fructofuranosidase according to the present invention, the transformant according to the present invention, or cultures obtained by culturing the transformant according to the present invention. The description about the same or equivalent constitution of the method for producing kestose according to the present invention as in the aforementioned improved β-fructofuranosidase, polypeptide, DNA, recombinant vector, transformant, and method for producing a improved β-fructofuranosidase according to the present invention will be omitted here.

Examples of the method for contacting sucrose with the improved β-fructofuranosidase according to the present invention can include a method which involves adding the improved β-fructofuranosidase to a solution containing sucrose, and leaving the mixture standing at 20° C. to 60° C. for approximately 20 hours. Examples of the method for contacting sucrose with the transformant according to the present invention when the host is *E. coli* can include a method which involves adding the transformant according to the present invention to a solution containing sucrose, followed by shake culture at 50° C. for several days.

Examples of the method for contacting sucrose with cultures obtained by culturing the transformant according to the present invention can include a method which involves adding the cultures obtained by culturing the transformant according to the present invention to a solution containing sucrose, and leaving the mixture standing or shaking the mixture at 20° C. to 60° C. for approximately 20 hours. In this context, the cultures according to the present invention may or may not be some treatment such as homogenization, grinding, suspension in a buffer solution, freezing-thawing, ultrasonication, centrifugation, heat treatment, salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, or isoelectric focusing electrophoresis.

Finally, the present invention provides a method for producing lactosucrose. The method for producing lactosucrose according to the present invention comprises a step of contacting a carbohydrate containing a terminal fructose residue and lactose with the following improved β-fructofuranosidase (I), the following transformant (II), or the following cultures (III):

(I) an improved β-fructofuranosidase comprising the following amino acid sequence (c) or (d):

(c) an amino acid sequence derived from the amino acid sequence of wild-type β-fructofuranosidase represented by SEQ ID NO: 2 by the introduction of one or two amino acid mutations selected from the following i) and iii):

i) an amino acid mutation that replaces leucine (L) at position 123 counted from the N terminus with cysteine (C), and iii) an amino acid mutation that replaces phenylalanine (F) at position 473 counted from the N terminus with tyrosine (Y); and (d) an amino acid sequence derived from the amino acid sequence (c) by the deletion, substitution, insertion, or addition of one or several amino acids except for the mutated amino acid, and having β fructofuranosidase activity;

(II) a transformant obtained by transferring a DNA encoding the improved β fructofuranosidase (I) or a recombinant vector comprising the DNA to a host; and (III) cultures obtained by culturing the transformant (II).

The description about the same or equivalent constitution of the method for producing lactosucrose according to the present invention as in the aforementioned improved β-fructofuranosidase, polypeptide, DNA, recombinant vector, transformant, method for producing a improved β-fructofuranosidase, and method for producing kestose according to the present invention will be omitted here.

Examples of the method for contacting a carbohydrate containing a terminal fructose residue and lactose with the improved β-fructofuranosidase (I) can include a method which involves adding the improved β-fructofuranosidase (I) to a solution containing a carbohydrate containing a terminal fructose residue and lactose, and leaving the mixture standing at 20° C. to 60° C. for approximately 20 hours. Examples of the method for contacting a carbohydrate containing a terminal fructose residue and lactose with the transformant (II) when the host is E. coli can include a method which involves adding the transformant according to the present invention to a solution containing a carbohydrate containing a terminal fructose residue and lactose, followed by shake culture at 50° C. for several days.

Examples of the method for contacting a carbohydrate containing a terminal fructose residue and lactose with the cultures (III) can include a method which involves adding the cultures (III) to a solution containing a carbohydrate containing a terminal fructose residue and lactose, and leaving the mixture standing or shaking the mixture at 20° C. to 60° C. for approximately 20 hours.

The method for producing kestose or the method for producing lactosucrose according to the present invention may have an additional step without impairing the features of the method for producing kestose or the method for producing lactosucrose according to the present invention, and may have, for example, a step of separating kestose by chromatography, a crystallization step such as boiling down crystallization, a drying step, a washing step, a filtration step, a sterilization step, and a step of adding a food additive.

Hereinafter, the improved β-fructofuranosidase, the polypeptide, the DNA, the recombinant vector, the transformant, the method for producing a improved β-fructofuranosidase, the method for producing kestose, and the method for producing lactosucrose according to the present invention will be described with reference to each Example. The technical scope of the present invention is not intended to be limited by the features indicated by these Examples.

EXAMPLES

<Example 1> Determination of Nucleotide Sequence of B. Indica-Derived Wild-Type β-Fructofuranosidase A gene of a β-fructofuranosidase of Beijerinckia indica subsp. indica NBRC3744 (hereinafter, abbreviated to "B. Indica") was cloned. Specifically, the genomic DNA of B. Indica was first extracted according to a routine method. Subsequently, primers of SEQ ID NO: 3 and SEQ ID NO: 4 given below were designed. Subsequently, the DNA encoding the B. Indica derived wild-type β fructofuranosidase was amplified by polymerase chain reaction (PCR) under conditions given below. Also, the full-length nucleotide sequence of the DNA encoding the B. Indica-derived wild-type β-fructofuranosidase was determined according to a routine method. The full-length nucleotide sequence of the DNA encoding the B. Indica-derived wild-type β-fructofuranosidase is shown in SEQ ID NO: 1, and the amino acid sequence of the B. Indica-derived wild-type β-fructofuranosidase encoded thereby is shown in SEQ ID NO: 2.

<<PCR Conditions for Amplification of DNA Encoding B. Indica-Derived Wild-Type β-Fructofuranosidase>>

Template: genomic DNA of B. Indica

```
Forward primer:
                                     (SEQ ID NO: 3)
5'-atggcaagtcgatcgtttaatgtttgtatac-3'

Reverse primer:
                                     (SEQ ID NO: 4)
5'-tttaccagactcgagttactggccgttcgtgac-3'
```

Enzyme for PCR: KOD-Plus-(Toyobo Co., Ltd.)

Reaction conditions: 30 cycles each involving 95° C. for 10 seconds, 60° C. for 20 seconds, and 68° C. for 2 minutes.

Subsequently, a signal sequence was predicted using the SignalP 4.1 server (http://www.cbs.dtu.dk/services/SignalP/) with reference to the nucleotide sequence of a DNA encoding a β-fructofuranosidase of Beijerinckia indica subsp. indica ATCC9039 (genomic DNA; GenBank: CP001016.1). As a result, the signal sequence was found to correspond to positions 1 to 28 in the amino acid sequence (SEQ ID NO: 2) of the B. Indica-derived wild-type β-fructofuranosidase.

<Example 2> Construction of β Fructofuranosidase Expression System (1) E. coli Intracellular Expression System

[1-1] Construction of Recombinant Vector

First, the DNA encoding the B. Indica derived wild-type β-fructofuranosidase was amplified by PCR under conditions given below.

<<PCR Conditions for Amplification of DNA Encoding B. Indica-Derived Wild-Type β-Fructofuranosidase>>

Template: genomic DNA of B. Indica

```
Forward primer:
                                     (SEQ ID NO: 5)
5'-ccgcgcggcagccatggttacccgataccgactccgcattcggg
acaagcctatgatcc-3'

Reverse primer:
                                     (SEQ ID NO: 6)
5'-gtggtggtgctcgagttactggccgttcgtgacaccatggccat
taccttggccaagcgcgggaagat-3'
```

Enzyme for PCR: KOD-Plus-(Toyobo Co., Ltd.)

Reaction conditions: 30 cycles each involving 95° C. for 10 seconds, 60° C. for 20 seconds, and 68° C. for 2 minutes Subsequently, the DNA of a pET28a plasmid was amplified by PCR under conditions given below.

<<PCR Conditions for Amplification of DNA of pET28a Plasmid>>

Template: pET28a plasmid (Merck KGaA)

```
Forward primer:
                                     (SEQ ID NO: 7)
5'-ctcgagcaccaccaccaccactga-3'
```

-continued

Reverse primer:
(SEQ ID NO: 8)
5'-atggctgccgcgcggcaccaggccgct-3'

Enzyme for PCR: KOD-Plus-(Toyobo Co., Ltd.)
Reaction conditions: 30 cycles each involving 95° C. for 10 seconds, 60° C. for 20 seconds, and 68° C. for 6 minutes The amplified DNA fragment encoding the *B. Indica* derived wild-type β fructofuranosidase and the amplified DNA fragment of the pET28a plasmid were ligated using In-Fusion HD Cloning Kit (Takara Bio Inc.) so that the DNA encoding the *B. Indica*-derived wild-type β-fructofuranosidase was inserted to the pET28a plasmid. The resulting vector was designated as a pET28a-*indica* recombinant vector.

[1-2] Transformation and Culture and Recovery of Transformant

The pET28a-*indica* recombinant vector was transferred to *E. coli* BL21 (DE3) competent cells (Cosmo Bio Co., Ltd.) to obtain recombinant *E. coli* as a transformant. This transformant was plate-cultured at 37° C. for 20 hours. Then, clones of the recombinant *E. coli* were picked up, inoculated to 1 mL of M9 SEED medium, and shake-cultured at 220 rpm at 30° C. for 18 hours. Subsequently, a 10 μL aliquot of the cultures was inoculated to 2 mL of M9 Main medium and shake-cultured at 220 rpm at 25° C. for 24 hours. Then, the cultures were centrifuged at 3500 rpm for 10 minutes to recover recombinant *E. coli*. The composition of the M9 SEED medium and the M9 Main medium is shown below.

M9 SEED medium (a total of 100 mL): 72 mL of water, 20 mL of 5×M9 salt, 5 mL of 20% casamino acid, 2 mL of 20% D-glucose, 1 mL of 2 mg/mL thymine, 0.2 mL of 50 mM $CaCl_2$, 40 μL of 2.5 M $MgCl_2$, 28 μL of 100 mg/mL $FeSO_4$, and 120 μL of 25 mg/mL kanamycin salt M9 Main medium (a total of 100 mL): 67 mL of water, 20 mL of 5×M9 salt, 5 mL of 20% casamino acid, 1 mL of 2 mg/mL thymine, 0.2 mL of 50 mM $CaCl_2$, 28 μL of 100 mg/mL $FeSO_4$, 2 mL of Overnight Express Autoinduction System 1 (O.N.E.; Merck KGaA) Sol. 1, 5 mL of O.N.E. Sol. 2, 100 μL of O.N.E. Sol. 3, and 120 μL of 25 mg/mL kanamycin salt

[1-3] Confirmation of β-Fructofuranosidase Activity 0.5 mL of BugBuster (Novagen/Merck KGaA) was added to the recombinant *E. coli* of this Example 2(1) [1-2], and the bacterial cells were left standing at 37° C. for 30 minutes and thereby homogenized for protein extraction. Then, a supernatant was recovered by centrifugation at 12000 rpm for 30 minutes and used as crude β-fructofuranosidase solution. Subsequently, a kestose formation reaction solution having composition given below was prepared and left standing at 37° C. or 50° C. for 22 hours to perform kestose formation reaction.

<<Composition of Kestose Formation Reaction Solution>>

20 (w/w) % aqueous sucrose solution: 450 μL 0.2 M phosphate buffer; 25 μL

Crude β-fructofuranosidase solution: 25 μL

Then, the kestose formation reaction solution was subjected to HPLC under conditions given below to confirm the proportion of each saccharide (fructose, glucose, sucrose, kestose, nystose, and other saccharides) contained in the kestose formation reaction solution, and the amounts of kestose and nystose. The proportion of each saccharide was calculated in percentage as a ratio of the area of each peak to the total area of all peaks detected. The amounts of kestose and nystose were calculated by multiplying the mass of sucrose in the kestose formation reaction solution by the respective proportions of kestose and nystose.

<<HPLC Conditions>>
Column: Cosmosil Sugar D 4.6×150 mm
Mobile phase: A: $H_2O$, B: 75% aqueous acetonitrile solution (0 to 6 min. and 8 to 11 min.) and 50% aqueous acetonitrile solution (6 to 8 min.)
Flow rate: 1.5 mL/min
Injection volume: 2.5 μL
Temperature: 25° C.
Detection: Corona Charged Aerosol Detector (CAD; Nippon Dionex K.K.), range: 500 pA As a result, the amount of kestose contained in the kestose formation reaction solution was equal to or smaller than the detection limit or was very small, demonstrating that kestose was hardly formed. From these results, the *E. coli* intracellular expression system of the β-fructofuranosidase was found to be unsuitable for kestose formation.

(2) *E. coli* Cell Surface Expression System
[2-1] Cell Surface Presentation by PgsA Anchor Protein
<2-1-1> Construction of Recombinant Vector A DNA encoding a PgsA anchor protein (GenBank: AB016245.1) of *Bacillus subtilis* (IAM1026, ATCC9466) was amplified by PCR under conditions given below. The obtained PCR product was digested with restriction enzymes NdeI and BglII according to a routine method. This fragment was used as a PgsA-DNA fragment.

<<PCR Conditions for Amplification of DNA Encoding PgsA Anchor Protein>>

Template: genomic DNA of *Bacillus subtilis* (IAM1026, ATCC9466)

Forward primer (NdeI site is underlined):
(SEQ ID NO: 9)
5'-aaacatatgaaaaaagaactgagctttcatg-3'

Reverse primer (BglII site is underlined):
(SEQ ID NO: 10)
5'-aaaagatctttagattttagtttgtcactatg-3'

Enzyme for PCR: KOD-Plus-(Toyobo Co., Ltd.)
Reaction conditions: 30 cycles each involving 95° C. for 10 seconds, 60° C. for 20 seconds, and 68° C. for 2 minutes The nucleotide sequence of the PgsA-DNA fragment was confirmed according to a routine method. The confirmed nucleotide sequence of the DNA encoding the PgsA anchor protein is shown in SEQ ID NO: 11, and the amino acid sequence of the PgsA anchor protein encoded thereby is shown in SEQ ID NO: 12.

Next, the DNA encoding the *B. Indica*-derived wild-type β-fructofuranosidase was amplified by PCR under conditions given below. The PCR product was digested with restriction enzymes BamHI and XhoI according to a routine method. This fragment was used as a *B. Indica*-derived wild-type β-fructofuranosidase DNA fragment.

<<PCR Conditions for Amplification of DNA Encoding *B. Indica*-Derived Wild-Type β-Fructofuranosidase>>

Template: genomic DNA of *B. Indica*

Forward primer (BamHI site is underlined):
(SEQ ID NO: 13)
5'-aaaggatcctcgggttacccgataccgactccgcattcgggaca-3'

Reverse primer (XhoI site is underlined):
(SEQ ID NO: 14)
5'-cccctcgagttactggccgttcgtgacaccatggccattaac-3'

Enzyme for PCR: KOD-Plus-(Toyobo Co., Ltd.)
Reaction conditions: 20 cycles each involving 95° C. for 10 seconds, 60° C. for 20 seconds, and 68° C. for 2 minutes Subsequently, the PgsA-DNA fragment and the *B. Indica*-derived wild-type β-fructofuranosidase DNA fragment were inserted to the NdeI site and the XhoI site of a pCDFDuet-1 plasmid (Merck KGaA) using DNA Ligation Kit Ver. 2.1

(Takara Bio Inc.) according to the attached instruction manual. The resulting vector was designated as a pCDF-*Indica* recombinant vector.

<2-1-2> Transformation and Culture and Recovery of Transformant

The pCDF-*Indica* recombinant vector of this Example 2(2) [2-1]<2-1-1> and a control pCDFDuet-1 plasmid were each transferred to *E. coli* by the method described in this Example 2(1) [1-2], and the obtained recombinant *E. coli* was cultured and recovered. However, the amount of the M9 SEED medium was set to 0.5 mL instead of 1 mL, and the culture time in the M9 SEED medium was set to 20 hours instead of 18 hours. Also, the antibiotic used was "100 μL of 50 mg/mL streptomycin sulfate" instead of "120 μL of 25 mg/mL kanamycin salt".

<2-1-3> Confirmation of β-Fructofuranosidase Activity

A kestose formation reaction solution having composition given below was prepared using the recombinant *E. coli* of this Example 2(2) [2-1]<2-1-2> and shaken at 220 rpm at 30° C. for 20 hours to perform kestose formation reaction. Then, a supernatant was recovered by centrifugation at 3500 rpm for 10 minutes. The recovered supernatant was diluted 100-fold by the addition of 50% acetonitrile and then subjected to HPLC under the conditions of this Example 2(1) [1-3]. The resulting HPLC chromatograms are shown in FIG. 1.

<<Composition of Kestose Formation Reaction Solution>>
20 (w/w) % aqueous sucrose solution: 430 μL
0.2 M phosphate buffer: 50 μL
Recombinant *E. coli*: whole amount As shown in the lower diagram of FIG. 1, no kestose was confirmed in the kestose formation reaction solution obtained using the recombinant *E. coli* harboring the pCDFDuet-1 plasmid. By contrast, as shown in the upper diagram of this figure, kestose was confirmed in the kestose formation reaction solution of the recombinant *E. coli* harboring the pCDF-*Indica* recombinant vector. These results demonstrated that *E. coli* presenting a β-fructofuranosidase on its cell surface can be used to form kestose.

[2-2] Cell Surface Presentation by CapA Anchor Protein

<2-2-1> Construction of Recombinant Vector

The PgsA anchor protein was searched using Basic Local Alignment Search Tool (BLAST) to extract a CapA anchor protein of a *Bacillus megaterium* DSM319 line having 55% identity to the PgsA anchor protein. An *E. coli* codon-optimized nucleotide sequence encoding the CapA anchor protein was designed and used as a capA_opti gene. The nucleotide sequence of the capA_opti gene is shown in SEQ ID NO: 15, and the amino acid sequence encoded thereby is shown in SEQ ID NO: 16.

Next, the DNA of the capA_opti gene was artificially synthesized, and a DNA encoding the CapA anchor protein was amplified by PCR under conditions given below using the synthesized DNA as a template. The obtained PCR product was used as a capA_opti-DNA fragment.

<<PCR Conditions for Amplification of DNA of CapA Sequence>>
Template: artificially synthesized DNA of capA_opti gene

```
Forward primer:
                                        (SEQ ID NO: 17)
5'-taagaaggagatatacatatgaaagaaaagaaactgaact
tccaag-3'

Reverse primer:
                                        (SEQ ID NO: 18)
5'-cgggtaacccgattgagatctatttgcctgggcttcgttc
tttttg-3'
```

Enzyme for PCR: KOD-Plus-(Toyobo Co., Ltd.)
Reaction conditions: 21 cycles each involving 94° C. for 15 seconds, 58° C. for 20 seconds, and 68° C. for 2 minutes Next, a DNA encoding an improved β-fructofuranosidase was amplified by inverse PCR under conditions given below. The obtained PCR product was used as an improved β-fructofuranosidase DNA fragment.

<<PCR Conditions for Amplification of DNA Encoding Improved β-Fructofuranosidase>>
Template: *Indica*-H395R/F473Y recombinant vector of Example 3(1) [1-1]

```
Forward primer:
                                        (SEQ ID NO: 19)
5'-agatctcaatcgggttacccgataccgac-3'

Reverse primer:
                                        (SEQ ID NO: 20)
5'-catatgtatatctccttcttatacttaac-3'
```

Enzyme for PCR: KOD-Plus-(Toyobo Co., Ltd.)
Reaction conditions: 35 cycles each involving 94° C. for 15 seconds and 68° C. for 6 minutes Subsequently, the capA_opti gene DNA fragment and the β-fructofuranosidase DNA fragment were ligated using In-Fusion HD Cloning Kit (Takara Bio Inc.) to obtain an *Indica*-H395R/F473Y recombinant vector having an insert of the DNA encoding the CapA anchor protein instead of the DNA encoding the PgsA anchor protein. This vector was designated as an *Indica*-CapA-H395R/F473Y recombinant vector.

<2-2-2> Transformation and Culture and Recovery of Transformant

The *Indica*-CapA-H395R/F473Y recombinant vector of this Example 2(2) [2-2]<2-2-1> and a control *Indica*-H395R/F473Y recombinant vector of Example 3(1) [1-1] were each transferred to *E. coli* by the method described in this Example 2(1) [1-2]. The obtained recombinant *E. coli* was cultured, and the transformant was recovered from 2 mL of the cultures.

<2-2-3> Confirmation of β-Fructofuranosidase Activity

A kestose formation reaction solution having composition given below was prepared using the recombinant *E. coli* of this Example 2(2) [2-2]<2-2-2>. This reaction solution was shaken at 200 rpm at 50° C. for 24 hours to perform kestose formation reaction. After the reaction, 100 μL of the kestose formation reaction solution was diluted 10-fold by the addition of 900 μL of ultrapure water. Then, an ion-exchange resin (Amberlite MB-4) was added thereto, and the mixture was stirred for 30 seconds to 1 minute. Subsequently, a supernatant was recovered by centrifugation at 14000×g for 5 minutes. This supernatant was subjected to HPLC under conditions given below. The proportion of each saccharide and the amount of kestose were calculated by the method described in this Example 2(1) [1-3]. The results are shown in Table 1 below. In Table 1, n.d. represents that the detected level was equal to or lower than the detection limit.

<<Composition of Kestose Formation Reaction Solution>>
60 (w/w) % sucrose solution (sucrose dissolved at 60 (w/w) % in 0.04 M phosphate buffer (pH 7)): 500 μL
Recombinant *E. coli*: whole amount <<HPLC Conditions>>
Column: TSKgel Amide-80 4.6×250 mm
Mobile phase: 70% aqueous acetonitrile solution
Flow rate: 1.0 mL/min
Injection volume: 20 μL
Temperature: 70° C.
Detection: differential refractive index detector (RID; Agilent Technologies, Inc.)

TABLE 1

| Recombinant vector | Cell surface presentation | Amount of kestose(mg) | Proportion (%) | | | | | |
|---|---|---|---|---|---|---|---|---|
| | | | Fructose | Glucose | Sucrose | Kestose | Nystose | Other saccharides |
| Indica-H395R/F473Y recombinant vector | PgsA anchor protein | 184.3 | 5.90 | 30.72 | 12.80 | 47.63 | n.d. | 2.95 |
| Indica-CapA-H395R/F473Y recombinant vector | CapA anchor protein | 196.7 | 4.78 | 29.26 | 12.56 | 50.83 | n.d. | 2.56 |

As shown in Table 1, kestose was formed while the amount of nystose was equal to or lower than the detection limit in the kestose formation reaction solution of the recombinant *E. coli* harboring the *Indica*-CapA-H395R/F473Y recombinant vector, as with the kestose formation reaction solution of the recombinant *E. coli* harboring the *Indica*-H395R/F473Y recombinant vector. These results demonstrated that *E. coli* presenting a β-fructofuranosidase on its cell surface using a PgsA anchor protein, a CapA anchor protein, or the like can be used to efficiently form kestose.

<Example 3> Preparation and Evaluation of Improved β-Fructofuranosidase (1) Preparation of Improved β Fructofuranosidase Single variants, double variants, and a triple variant of the β fructofuranosidase consisting of amino acid sequences were prepared and used as improved β-fructofuranosidases. Specific procedures will be shown below.

[1-1] Construction of Recombinant Vector

A DNA encoding each improved β-fructofuranosidase was first amplified by PCR under conditions given below.

<<PCR Conditions for Amplification of DNA Encoding Improved β-Fructofuranosidase>>

Template: As shown in Table 2

Forward primer and Reverse primer: As shown in Table 2

Enzyme for PCR: KOD-Plus-NEO (Toyobo Co., Ltd.)

Reaction conditions: 15 cycles each involving 95° C. for 1 minute, 95° C. for 10 seconds, 68° C. for 20 seconds, and 68° C. for 3.5 minutes

TABLE 2

| Type | Recombinant vector | Amino acid mutation | Template | Forward primer | Reverse primer |
|---|---|---|---|---|---|
| Single variant | Indica-L123C recombinant vector | L123C | pCDF-Indica recombinant vector | tgtaccgctgatccg catgccggttatgt (SEQ ID NO: 21) | cgagaaaatgacctc ccacccctggaagct (SEQ ID NO: 22) |
| | Indica-H395R recombinant vector | H395R | pCDF-Indica recombinant vector | cgtcgcacgacctat gcggcgggcgtcgat (SEQ ID NO: 23) | gctgatcgtgaacag gtaatattttccatc (SEQ ID NO: 24) |
| | Indica-H395K recombinant vector | H395K | pCDF-Indica recombinant vector | aaacgcacgacctat gcggcgggcgtcgat (SEQ ID NO: 25) | gctgatcgtgaacag gtaatattttccatc (SEQ ID NO: 26) |
| | Indica-F473Y recombinant vector | F473Y | pCDF-Indica recombinant vector | tatatcgatgccatc ggccctcgtcgcggt (SEQ ID NO: 27) | cgattcaacgaggcc gcccggcatgacata (SEQ ID NO: 28) |
| Double variant | Indica-H396R/L123C recombinant vector | H395R/L123C | H395R recombinant vector | tgtaccgctgatccg catgccggttatgt (SEQ ID NO: 29) | cgagaaaatgacctc ccacccctggaagct (SEQ ID NO: 30) |
| | Indica-H395R/F473Y recombinant vector | H395R/F473Y | H395R recombinant vector | tatatcgatgccatc ggccctcgtcgcggt (SEQ ID NO: 31) | cgattcaacgaggcc gcccggcatgacata (SEQ ID NO: 32) |
| | Indica-F473Y/L123C recombinant vector | F473Y/L123C | F473Y recombinant vector | tgtaccgctgatccg catgccggttatgt (SEQ ID NO: 33) | cgagaaaatgacctc ccacccctggaagct (SEQ ID NO: 34) |
| Triple variant | Indica-H395R/F473Y/L123C recombinant vector | H395R/F473Y/L123C | H395R/F473Y recombinant vector | tgtaccgctgatccg catgccggttatgt (SEQ ID NO: 35) | cgagaaaatgacctc ccacccctggaagct (SEQ ID NO: 36) | derived from the amino acid sequence (SEQ ID NO: 2) of the *B. Indica*-derived wild-type β-fructofuranosidase by the introduction of amino acid mutation(s) selected from amino acid mutations to respectively replace leucine (L) at position 123 counted from the N terminus with cysteine (C), histidine (H) at position 395 counted from the N terminus with arginine (R) or lysine (K), and phenylalanine (F) at position 473 counted from the N terminus with tyrosine (Y) (hereinafter, these amino acid mutations are abbreviated to "L123C", "H395R", "H395K", and "F473Y", respectively)

Subsequently, a restriction enzymes DpnI was added to each PCR product, and the PCR product was digested at 37° C. for 1 hour and then subjected to agarose gel electrophoresis. The gel was excised and purified. Ligation high (Toyobo Co., Ltd.) and T4 Polynucleotide Kinase (Toyobo Co., Ltd.) were added thereto and left standing at 16° C. for 1 hour for ligation to construct a recombinant vector.

As for the obtained single variant recombinant vectors, the recombinant vectors having inserts of the DNAs encoding the improved β-fructofuranosidases containing L123C, H395R, and F473Y, respectively, were designated as an Indica-L123C recombinant vector, an Indica-H395R recombinant vector, and an Indica-F473Y recombinant vector, respectively.

Likewise, as for the double variant recombinant vectors, the recombinant vectors having inserts of the DNAs encoding the improved β-fructofuranosidases containing H395R and L123C, H395R and F473Y, and F473Y and L123C, respectively, were designated as an Indica-H395R/L123C recombinant vector, an Indica-H395R/F473Y recombinant vector, and an Indica-F473Y/L123C recombinant vector, respectively.

As for the triple variant recombinant vector, the recombinant vector having an insert of the DNA encoding the improved β fructofuranosidase containing L123C, H395R, and F473Y was designated as an Indica-H395R/F473Y/L123C recombinant vector.

[1-2] Transformation and Culture and Recovery of Transformant

Each recombinant vector of this Example 3(1) [1-1] was transferred to E. coli JM109 competent cells, and recombinant E. coli was recovered, according to the method described in Example 2(1) [1-2]. Subsequently, a recombinant vector was recovered from the recombinant E. coli and transferred to E. coli BL21 (DE3) competent cells (Cosmo Bio Co., Ltd.) to obtain recombinant E. coli as a transformant. This transformant was plate-cultured at 37° C. for 20 hours. Then, clones of the recombinant E. coli were picked up, inoculated to 0.5 mL of M9 SEED medium, and shake-cultured at 800 rpm at 30° C. for 20 hours. Subsequently, a 5 μL aliquot of the cultures was inoculated to 2 mL of M9 Main medium and shake-cultured at 800 rpm at 25° C. for 23 hours. Then, the cultures were centrifuged at 3500 rpm for 10 minutes to recover recombinant E. coli.

(2) Evaluation of Improved β-Fructofuranosidase
[2-1] Confirmation of Kestose Formation Activity Kestose formation reaction was performed by the method described in Example 2(2) [2-2]<2-2-3> using each recombinant E. coli of this Example 3(1) [1-2] or a control recombinant E. coli harboring the pCDF-Indica recombinant vector of Example 2(2) [2-1]<2-1-2>, and each kestose formation reaction solution was subjected to HPLC. The results are shown in Table 3. In Table 3, n.d. represents that the detected level was equal to or lower than the detection limit.

As shown in Table 3, the amount of kestose was 39.7 mg in the kestose formation reaction solution of the recombinant E. coli harboring the pCDF-Indica recombinant vector, whereas the amount of kestose was 44.5 mg, 163.5 mg, 105.3 mg, 89.9 mg, 175.5 mg, 184.3 mg, 120.5 mg, and 218.8 mg in the kestose formation reaction solutions of the recombinant E. coli harboring the Indica-L123C recombinant vector, the Indica-H395R recombinant vector, the Indica-H395K recombinant vector, the Indica-F473Y recombinant vector, the Indica-H395R/L123C recombinant vector, the Indica-H395R/F473Y recombinant vector, the Indica-F473Y/L123C recombinant vector, and the Indica-H395R/F473Y/L123C recombinant vector, respectively.

The proportion of kestose was 10.25% in the kestose formation reaction solution of the recombinant E. coli harboring the pCDF-Indica recombinant vector, whereas the proportion of kestose was 11.50%, 42.26%, 27.20%, 23.23%, 45.34%, 47.63%, 31.13%, and 56.54% in the kestose formation reaction solutions of the recombinant E. coli harboring the Indica-L123C recombinant vector, the Indica-H395R recombinant vector, the Indica-H395K recombinant vector, the Indica-F473Y recombinant vector, the Indica-H395R/L123C recombinant vector, the Indica-H395R/F473Y recombinant vector, the Indica-F473Y/L123C recombinant vector, and the Indica-H395R/F473Y/L123C recombinant vector, respectively.

The proportion of nystose was 5.11% in the kestose formation reaction solution of the recombinant E. coli harboring the pCDF-Indica recombinant vector, whereas the proportion of nystose was 3.99%, n.d., 1.95%, 3.42%, n.d., n.d., 1.32%, and 0.07% in the kestose formation reaction solutions of the recombinant E. coli harboring the Indica-L123C recombinant vector, the Indica-H395R recombinant vector, the Indica-H395K recombinant vector, the Indica-F473Y recombinant vector, the Indica-H395R/L123C recombinant vector, the Indica-H395R/F473Y recombinant vector, the Indica-F473Y/L123C recombinant vector, and the Indica-H395R/F473Y/L123C recombinant vector, respectively.

The proportion of other saccharides was 9.02% in the kestose formation reaction solution of the recombinant E. coli harboring the pCDF-Indica recombinant vector, whereas the proportion of other saccharides was 3.52%, 2.41%, 3.28%, 8.37%, 0.32%, 2.95%, 1.68%, and 1.51% in

TABLE 3

| Type | Recombinant vector | Amino acid mutation | Amount of kestose(mg) | Proportion (%) | | | | | |
|---|---|---|---|---|---|---|---|---|---|
| | | | | Fructose | Glucose | Sucrose | Kestose | Nystose | Other saccharides |
| Control | pCDF-Indica recombinant vector | None (wild-type) | 39.7 | 10.24 | 59.05 | 6.33 | 10.25 | 5.11 | 9.02 |
| Single variant | Indica-L123C recombinant vector | L123C | 44.5 | 3.39 | 26.87 | 50.73 | 11.50 | 3.99 | 3.52 |
| | Indica-H395R recombinant vector | H395R | 163.5 | 9.03 | 35.27 | 11.04 | 42.26 | n.d. | 2.41 |
| | Indica-H395K recombinant vector | H395K | 105.3 | 13.43 | 40.19 | 13.96 | 27.20 | 1.95 | 3.28 |
| | Indica-F473Y recombinant vector | F473Y | 89.9 | 6.76 | 51.28 | 6.93 | 23.23 | 3.42 | 8.37 |
| Double variant | Indica-H395R/L123C recombinant vector | H395R/L123C | 175.5 | 2.35 | 19.99 | 31.99 | 45.34 | n.d. | 0.32 |
| | Indica-H395R/F473Y recombinant vector | H395R/F473Y | 184.3 | 5.90 | 30.72 | 12.80 | 47.63 | n.d. | 2.95 |
| | Indica-F473Y/L123C recombinant vector | F473Y/L123C | 120.5 | 2.45 | 26.53 | 36.89 | 31.13 | 1.32 | 1.68 |
| Triple variant | Indica-H395R/F473Y/L123C recombinant vector | H395R/F473Y/L123C | 218.8 | 1.77 | 22.52 | 17.60 | 56.54 | n.d. | 1.51 | the kestose formation reaction solutions of the recombinant *E. coli* harboring the *Indica*-L123C recombinant vector, the *Indica*-H395R recombinant vector, the *Indica*-H395K recombinant vector, the *Indica*-F473Y recombinant vector, the *Indica*-H395R/L123C recombinant vector, the *Indica*-H395R/F473Y recombinant vector, the *Indica*-F473Y/L123C recombinant vector, and the *Indica*-H395R/F473Y/L123C recombinant vector, respectively.

Specifically, the kestose formation reaction solutions of the recombinant *E. coli* harboring the *Indica*-L123C recombinant vector, the *Indica*-H395R recombinant vector, the *Indica*-H395K recombinant vector, the *Indica*-F473Y recombinant vector, the *Indica*-H395R/L123C recombinant vector, the *Indica*-H395R/F473Y recombinant vector, the *Indica*-F473Y/L123C recombinant vector, and the *Indica*-H395R/F473Y/L123C recombinant vector increased the amount of kestose, reduced both of the proportion of nystose and the proportion of other saccharides, and increased the proportion of kestose, as compared with the kestose formation reaction solution of the recombinant *E. coli* harboring the pCDF-*Indica* recombinant vector. From this, the kestose formation reaction mediated by the improved β-fructofuranosidase consisting of an amino acid sequence containing at least one of the amino acid mutations L123C, H395R, H395K, and F473Y was found to remarkably reduce the proportion of by-products such as nystose and improve the proportion of kestose, as compared with the kestose forma- <<Composition of Lactosucrose Formation Reaction Solution>>
Sucrose/lactose solution (sucrose and lactose dissolved at 22 (w/w) % and 18 (w/w) %, respectively, in 0.05 M phosphate buffer (pH 6.0)): 350 μL
Recombinant *E. coli*: whole amount This reaction solution was shaken at 220 rpm at 55° C. for 6 hours to perform lactosucrose formation reaction. After the reaction, 50 μL of the lactosucrose formation reaction solution was diluted by the addition of 450 μL of ultrapure water and 500 μL of acetonitrile and then heated at 35° C. for 10 minutes. Subsequently, a supernatant was recovered by centrifugation at 15000×g at 25° C. for 10 minutes and filtered through a filter. This filtrate was subjected to HPLC under conditions given below. The proportion of each saccharide and the amount of lactosucrose were calculated by the method described in Example 2(1) [1-3]. The results are shown in Table 4. In Table 4, n.d. represents that the detected level was equal to or lower than the detection limit.

<<HPLC Conditions>>
Column: TSKgel Amide-80 4.6×250 mm
Mobile phase: 70% aqueous acetonitrile solution
Flow rate: 1.0 mL/min
Injection volume: 20 μL
Temperature: 35° C.
Detection: differential refractive index detector (RID; Showa Denko K.K.)

TABLE 4

| | | | | Proportion(%) | | | | | |
| | | | | | Monosaccharide | Disaccharide | | Trisaccharide | | Other |
| Type | Recombinant vector | Amino acid mutation | Amount of lactosucrose (mg) | Glucose fructose | Sucrose | Lactose | Kestose | Lactosucrose | saccharides |
|---|---|---|---|---|---|---|---|---|---|
| Control | pCDF-Indica recombinant vector | None (wild-type) | 29.4 | 29.9 | 12.8 | 32.2 | 5.8 | 17.8 | 1.5 |
| Single variant | Indica-L123C recombinant vector | L123C | 54.8 | 14.4 | 28.4 | 22.9 | 0.9 | 33.2 | 0.2 |
| | Indica-F473Y recombinant vector | F473Y | 45.6 | 20.4 | 21.9 | 24.7 | 4.8 | 27.6 | 0.6 | tion reaction mediated by the wild-type β-fructofuranosidase, resulting in increase in the amount of kestose.

These results demonstrated that a β-fructofuranosidase that can efficiently form kestose in a large amount while reducing the rate of formation of by-products such as nystose can be obtained by introducing at least one amino acid mutation selected from amino acid mutations that respectively replace leucine (L) at position 123 counted from the N terminus with cysteine (C), histidine (H) at position 395 counted from the N terminus with arginine (R) or lysine (K), and phenylalanine (F) at position 473 counted from the N terminus with tyrosine (Y), to the amino acid sequence (SEQ ID NO: 2) of the wild-type β-fructofuranosidase.

[2-2] Confirmation of Lactosucrose Formation Activity

A lactosucrose formation reaction solution having composition given below was prepared using the recombinant *E. coli* harboring the *Indica*-L123C recombinant vector or the *Indica*-F473Y recombinant vector of this Example 3(1) [1-2], or a control recombinant *E. coli* harboring the pCDF-*Indica* recombinant vector of Example 2(2) [2-1]<2-1-2>. However, the recombinant *E. coli* was used in the whole amount recovered from 0.5 mL of cultures. Also, the recovery of the recombinant *E. coli* from the cultures was performed by the centrifugation of the cultures at 15000×g at 4° C. for 10 minutes.

A shown in Table 4, the amount of lactosucrose was 29.4 mg in the lactosucrose formation reaction solution of the recombinant *E. coli* harboring the pCDF-*Indica* recombinant vector, whereas the amount of lactosucrose was 54.8 mg and 45.6 mg in the lactosucrose formation reaction solutions of the recombinant *E. coli* harboring the *Indica*-L123C recombinant vector and the *Indica*-F473Y recombinant vector, respectively. The proportion of lactosucrose was 17.8% in the lactosucrose formation reaction solution of the recombinant *E. coli* harboring the pCDF-*Indica* recombinant vector, whereas the proportion of lactosucrose was 33.2% and 27.6% in the lactosucrose formation reaction solutions of the recombinant *E. coli* harboring the *Indica*-L123C recombinant vector and the *Indica*-F473Y recombinant vector, respectively.

Specifically, the lactosucrose formation reaction solutions of the recombinant *E. coli* harboring the *Indica*-L123C recombinant vector and the *Indica*-F473Y recombinant vector remarkably increased the amount of lactosucrose and the proportion of lactosucrose, as compared with the lactosucrose formation reaction solution of the recombinant *E. coli* harboring the pCDF-*Indica* recombinant vector. From this, the lactosucrose formation reaction mediated by the improved β-fructofuranosidase consisting of an amino acid sequence containing at least one of the amino acid mutations L123C and F473Y was found to increase the proportion of lactosucrose and the amount of lactosucrose, as compared with the lactosucrose formation reaction mediated by the wild-type β-fructofuranosidase.

These results demonstrated that a β-fructofuranosidase that can efficiently form lactosucrose in a large amount can be obtained by introducing at least one amino acid mutation selected from amino acid mutations that respectively replace leucine (L) at position 123 counted from the N terminus with cysteine (C) and phenylalanine (F) at position 473 counted from the N terminus with tyrosine (Y), to the amino acid sequence (SEQ ID NO: 2) of the wild-type β-fructofuranosidase.

<Example 4> Preparation and Evaluation of Improved β-Fructofuranosidase for β-Fructofuranosidase Homologous to *B. Indica* Derived Wild Type β Fructofuranosidase (1) Alignment β-fructofuranosidases (i) and (ii) given below were extracted as a β-fructofuranosidase consisting of an amino acid sequence having 75% identity to the *B. Indica*-derived wild-type β-fructofuranosidase and a β-fructofuranosidase consisting of an amino acid sequence having 66% identity to the *B. Indica*-derived wild-type β-fructofuranosidase, respectively. Their identity to an amino acid sequence (which corresponds to positions 29 to 534 of SEQ ID NO: 2) except for a signal sequence (which corresponds to positions 1 to 28 of SEQ ID NO: 2) in the amino acid sequence of the *B. Indica*-derived wild-type β-fructofuranosidase is indicated within the parentheses.

(i) 75% identity (identity excluding the signal sequence: 76%): β-fructofuranosidase (GenBank: ACC75109.1) of *Burkholderia phymatum* STM815 (hereinafter, abbreviated to "Burk")

(ii) 66% identity (identity excluding the signal sequence: 65%): β-fructofuranosidase (GenBank: AAB36606.1) of *Gluconacetobacter diazotrophicus* SRT4 (hereinafter, abbreviated to "Glucono")

Next, the amino acid sequence (SEQ ID NO: 2) of the *B. Indica*-derived wild-type β-fructofuranosidase was aligned with the amino acid sequences of the β-fructofuranosidases (i) and (ii) by the Clustal W method (http://www.genome.jp/tools/clustalw/). As a result, histidine (H) at position 395 counted from the N terminus in the amino acid sequence of the *B. Indica*-derived wild-type β-fructofuranosidase was found to correspond to histidine (H) at position 393 counted from the N terminus in the β fructofuranosidase (i) and histidine (H) at position 419 counted from the N terminus in the β fructofuranosidase (ii).

(2) Construction of Recombinant Vector

[2-1] Construction of Recombinant Vector Having Insert of DNA Encoding Wild-Type β-Fructofuranosidase A DNA encoding the Burk-derived wild-type β-fructofuranosidase was amplified by PCR under conditions given below. The obtained PCR product was used as a Burk wild-type DNA fragment. The nucleotide sequence of the DNA encoding the Burk-derived wild-type β-fructofuranosidase is shown in SEQ ID NO: 37, and the amino acid sequence of the Burk-derived wild-type β-fructofuranosidase encoded thereby is shown in SEQ ID NO: 38.

<<PCR Conditions for Amplification of DNA Encoding Burk-Derived Wild-Type β-Fructofuranosidase>>

Template: genomic DNA of Burk

Forward primer:
(SEQ ID NO: 39)
5'-aaactaaaatctaaaagatctcagactgcaacgccaggcttc
cccg-3'

Reverse primer:
(SEQ ID NO: 40)
5'-ggtttctttaccagactcgagttactggctgttgccgccctg
cccgtttcc-3'

Enzyme for PCR: KOD-Plus-(Toyobo Co., Ltd.)

Reaction conditions: 21 cycles each involving 94° C. for 15 seconds, 58° C. for 20 seconds, and 68° C. for 2 minutes Also, an *E. coli* codon-optimized nucleotide sequence encoding the amino acid sequence of the Glucono β-fructofuranosidase (GenBank: AAB36606.1) was designed and used as a Glucono_opti gene. The nucleotide sequence of the Glucono_opti gene is shown in SEQ ID NO: 41, and the amino acid sequence encoded thereby is shown in SEQ ID NO: 42.

Next, the DNA of the Glucono_opti gene was artificially synthesized, and a DNA encoding the Glucono-derived wild-type β-fructofuranosidase was amplified by PCR under conditions given below using the synthesized DNA as a template. The obtained PCR product was used as a Glucono wild-type DNA fragment.

<<PCR Conditions for Amplification of DNA Encoding Glucono-Derived Wild-Type β-Fructofuranosidase>>

Template: artificially synthesized DNA of Glucono_opti gene

Forward primer:
(SEQ ID NO: 43)
5'-aaactaaaatctaaaagatctcaaggcaattttctcgccag
gaag-3'

Reverse primer:
(SEQ ID NO: 44)
5'-ggtttctttaccagactcgagttattgattcagaaattgacg
gacctgt-3'

Enzyme for PCR: KOD-Plus-(Toyobo Co., Ltd.)

Reaction conditions: 21 cycles each involving 94° C. for 15 seconds, 58° C. for 20 seconds, and 68° C. for 2 minutes Next, the DNA of the pCDFDuet-1 plasmid having an insert of the DNA encoding the PgsA anchor protein was amplified by PCR under conditions given below. The obtained PCR product was used as a pCDF-PgsA-DNA fragment.

<<PCR Conditions for Amplification of DNA of pCDF-Duet-1 Having Insert of DNA Encoding PgsA Anchor Protein>>

Template: pCDF-*Indica* recombinant vector of Example 2(2) [2-1]<2-1-1>

Forward primer:
(SEQ ID NO: 45)
5'-tctggtaaagaaaccgctgctgcgaaattt-3'

Reverse primer:
(SEQ ID NO: 46)
5'-tttagattttagtttgtcactatgatcaat-3'

The Burk wild-type DNA fragment and the pCDF-PgsA-DNA fragment or the Glucono wild-type DNA fragment and the pCDF-PgsA-DNA fragment were ligated using In-Fusion HD Cloning Kit (Takara Bio Inc.) to obtain recombinant vectors. The former recombinant vector was designated as a pCDF-Burk recombinant vector, and the latter recombinant vector was designated as a pCDF-Glucono recombinant vector.

[2-2] Construction of Recombinant Vector Having Insert of DNA Encoding Improved β-Fructofuranosidase Recombinant vectors having inserts of DNAs encoding improved β-fructofuranosidases (single variants) consisting of amino acid sequences containing an amino acid mutation that replaces a histidine residue at position 393 counted from the N terminus in the amino acid sequence of the Burk-derived wild-type β-fructofuranosidase or histidine (H) at position 419 counted from the N terminus in the amino acid sequence of the Glucono-derived wild-type β-fructofuranosidase with arginine (R) (hereinafter, these amino acid mutations are abbreviated to "Burk-H393R" and "Glucono-H419R", respectively) were prepared by the method of Example 3(1) [1-1]. However, the PCR templates and primers used are as described in Table 5.

As for the obtained single variant recombinant vectors, the recombinant vectors having inserts of the DNAs encoding the improved β-fructofuranosidases consisting of amino acid sequences containing Burk-H393R and Glucono-H419R, respectively, were designated as a Burk-H393R recombinant vector and a Glucono-H419R recombinant vector, respectively.

As shown in Table 6, the amount of kestose was 57.6 mg, 56.8 mg, and 39.7 mg in the kestose formation reaction solutions of the recombinant *E. coli* harboring the pCDF-Burk recombinant vector, the pCDF-Glucono recombinant vector, and the pCDF-*Indica* recombinant vector, respectively, whereas the amount of kestose was 106.4 mg, 60.3 mg, and 163.5 mg in the kestose formation reaction solutions of the recombinant *E. coli* harboring the Burk-H393R recombinant vector, the Glucono-H419R recombinant vector, and the *Indica*-H395R recombinant vector, respectively, and was thus increased in all of these reaction solutions.

The proportion of kestose was 14.87%, 14.67%, and 10.25% in the kestose formation reaction solutions of the recombinant *E. coli* harboring the pCDF-Burk recombinant vector, the pCDF-Glucono recombinant vector, and the pCDF-*Indica* recombinant vector, respectively, whereas the proportion of kestose was 27.49%, 15.59%, and 42.26% in the kestose formation reaction solutions of the recombinant

TABLE 5

| Type | Recombinant vector | Amino acid mutations | Template | Forward primer | Reverse primer |
|---|---|---|---|---|---|
| Single variant | Burk-H393R recombinant vector | Burk-H393R | pCDF-Burk recombinant vector | cgtcgcacaacgatg gcagcaggcgttgac (SEQ ID NO: 47) | gctgatcgtgaacag gtagtacttgccgtc (SEQ ID NO: 48) |
| | Glucono-H419R recombinant vector | Glucono-H419R | pCDF-Glucono recombinant vector | cgtcgcaccaccttt gcggcgggtgtgga (SEQ ID NO: 49) | gctgatcgtgaagat gtagtacttgccgtt (SEQ ID NO: 50) |

(3) Confirmation of β-Fructofuranosidase Activity

The pCDF-Burk recombinant vector and the pCDF-Glucono recombinant vector of this Example 4(2) [2-1] and the Burk-H393R recombinant vector and the Glucono-H419R recombinant vector of this Example 4(2) [2-2] were each transferred to *E. coli* by the method of Example 3(1) [1-2]. Each obtained recombinant *E. coli* was cultured, and the transformant was recovered from 2 mL of cultures. Subsequently, the amount of kestose formed and the amount of nystose formed were measured by the method of Example 2(2) [2-2]<2-2-3> using the resulting recombinant *E. coli*. The results are shown in Table 6. For comparison, the results about the recombinant *E. coli* harboring the pCDF-*Indica* recombinant vector or the *Indica*-H395R recombinant vector among the results shown in Table 3 are also shown in the lower two columns of Table 6. In Table 6, n.d. represents that the detected level was equal to or lower than the detection limit.

*E. coli* harboring the Burk-H393R recombinant vector, the Glucono-H419R recombinant vector, and the *Indica*-H395R recombinant vector, respectively, and was thus increased in all of these reaction solutions.

The proportion of nystose was 4.53%, 5.03%, and 5.11% in the kestose formation reaction solutions of the recombinant *E. coli* harboring the pCDF-Burk recombinant vector, the pCDF-Glucono recombinant vector, and the pCDF-*Indica* recombinant vector, respectively, whereas the proportion of nystose was n.d., 0.23%, and n.d. in the kestose formation reaction solutions of the recombinant *E. coli* harboring the Burk-H393R recombinant vector, the Glucono-H419R recombinant vector, and the *Indica*-H395R recombinant vector, respectively, and was thus decreased in all of these reaction solution.

The proportion of other saccharides was 3.26%, 4.46%, and 9.02% in the kestose formation reaction solutions of the recombinant *E. coli* harboring the pCDF-Burk recombinant

TABLE 6

| | | | | Proportion(%) | | | | | |
|---|---|---|---|---|---|---|---|---|---|
| Type | Recombinant vector | Amino acid mutation | Amount of kestose | Fructose | Glucose | Sucrose | Kestose | Nystose | Other saccharides |
| Burk-derived | pCDF-Burk recombinant vector | None (wild-type) | 57.6 | 6.39 | 32.79 | 38.15 | 14.87 | 4.53 | 3.26 |
| | Burk-H393R recombinant vector | Burk-H393R | 106.4 | 7.67 | 25.10 | 38.93 | 27.49 | n.d. | 0.82 |
| Glucono-derived | pCDF-Glucono recombinant vector | None (wild-type) | 56.8 | 6.18 | 32.80 | 36.86 | 14.67 | 5.03 | 4.46 |
| | Glucono-H419R recombinant vector | Glucono-H419R | 60.3 | 12.57 | 29.57 | 41.06 | 15.59 | 0.23 | 0.99 |
| B. Indica-derived | pCDF-Indica recombinant vector | None (wild-type) | 39.7 | 10.24 | 59.05 | 6.33 | 10.25 | 5.11 | 9.02 |
| | Indica-H395R recombinant vector | H395R | 163.5 | 9.03 | 35.27 | 11.04 | 42.26 | n.d. | 2.41 | vector, the pCDF-Glucono recombinant vector, and the pCDF-*Indica* recombinant vector, respectively, whereas the proportion of other saccharides was 0.82%, 0.99%, and 2.41% in the kestose formation reaction solutions of the recombinant *E. coli* harboring the Burk-H393R recombinant vector, the Glucono-H419R recombinant vector, and the *Indica*-H395R recombinant vector, respectively, and was thus decreased in all of these reaction solution.

Specifically, the kestose formation reaction mediated by the improved β-fructofuranosidase consisting of an amino acid sequence containing Burk-H393R, Glucono-H419R, or H395R was found to increase the amount of kestose, reduce both of the proportion of nystose and the proportion of other saccharides, and increase the proportion of kestose, as compared with the kestose formation reaction mediated by the wild-type β-fructofuranosidase lacking these amino acid mutations.

These results demonstrated that a improved β-fructofuranosidase that can efficiently form kestose in a large amount while reducing the rate of formation of by-products such as nystose can be obtained by introducing an amino acid mutation that replaces histidine (H) corresponding to position 395 counted from the N terminus in the amino acid sequence (SEQ ID NO: 2) of the *B. Indica*-derived wild-type β-fructofuranosidase in alignment with arginine (R) or lysine (K), to an amino acid sequence of a β-fructofuranosidase comprising an amino acid sequence having 60% or higher identity to the amino acid sequence (SEQ ID NO: 2) of the *B. Indica*-derived wild-type β-fructofuranosidase.

The invention claimed is:

1. An improved β-fructofuranosidase comprising an amino acid sequence having 60% or higher identity to the amino acid sequence of SEQ ID NO: 2, wherein the amino acid sequence of the improved β-fructofuranosidase contains an amino acid mutation that replaces histidine (H) corresponding to position 395 counted from the N terminus of SEQ ID NO: 2 in alignment with arginine (R) or lysine (K).

2. An improved β-fructofuranosidase comprising the amino acid sequence of SEQ ID NO: 2, wherein the amino acid sequence contains one or more amino acid mutations selected from the group consisting of:
 i) an amino acid mutation that replaces leucine (L) at position 123 counted from the N terminus with cysteine (C),
 ii) an amino acid mutation that replaces histidine (H) at position 395 counted from the N terminus with arginine (R) or lysine (K), and
 iii) an amino acid mutation that replaces phenylalanine (F) at position 473 counted from the N terminus with tyrosine (Y).

3. A DNA encoding the improved β-fructofuranosidase according to claim 1.

4. A recombinant vector comprising the DNA according to claim 3.

5. A transformant obtained by transformation with the DNA according to claim 3.

6. The transformant according to claim 5, wherein the host is *E. coli*.

7. A method for producing an improved β-fructofuranosidase, comprising a step of obtaining an improved β-fructofuranosidase from cultures obtained by culturing the transformant according to claim 6.

8. A method for producing kestose, comprising a step of contacting sucrose with the improved β-fructofuranosidase according to claim 1.

9. A method for producing kestose, comprising a step of contacting sucrose with the transformant according to claim 5.

10. A method for producing kestose, comprising a step of contacting sucrose with cultures obtained by culturing the transformant according to claim 5.

11. A DNA encoding the improved β-fructofuranosidase according to claim 2.

12. A recombinant vector comprising the DNA according to claim 11.

13. A transformant obtained by transformation with the DNA according to claim 11.

14. The transformant according to claim 13, wherein the host is *E. coli*.

15. A method for producing an improved β-fructofuranosidase, comprising a step of obtaining an improved β-fructofuranosidase from cultures obtained by culturing the transformant according to claim 13.

16. A method for producing kestose, comprising a step of contacting sucrose with the improved β-fructofuranosidase according to claim 2.

17. A method for producing kestose, comprising a step of contacting sucrose with the transformant according to claim 13.

18. A method for producing kestose, comprising a step of contacting sucrose with cultures obtained by culturing the transformant according to claim 13.

\* \* \* \* \*

SEQUENCE LISTING

```
<160> NUMBER OF SEQ ID NOS: 50

<210> SEQ ID NO 1
<211> LENGTH: 1605
<212> TYPE: DNA
<213> ORGANISM: Beijerinckia indica

<400> SEQUENCE: 1
atggcaagtc gatcgtttaa tgtttgtata cgtagcctca tcgcgggctc gcttctgact      60
gccacagcac tgtccgctca ggctcaatcg ggttacccga taccgactcc gcattcggga     120
caagcctatg atccatttgc agattttacc gccaaatgga cgcgcgccaa tgcccgtcaa     180
atcaaggcgc aatcacatgt cccggtgtca cccgatcaga attcgctgcc gctcaatctg     240
acgatgcccg atatccctgc cgatttcccg caaaccaacc cggacgtgtg ggtgtgggat     300
acgtggcctc tcgccgatgt gcatggcaat cagctgagct tccaggggtg ggaggtcatt     360
ttctcgctga ccgctgatcc gcatgccggt tatgttttcg atgatcgcca cgttcacgca     420
cgtatcggct tcttttatcg caaggccgga attcccgcga accagcgccc gattgatggc     480
ggctggatct atggcgggca tttgttcccg gatggtagca gcgtcaaagt cttcggtaac     540
gtccccatga cgcaaaacgc ggaatggtcc ggcggcgccc gcttcgtggg cggcccttat     600
gctgatggcc cgcaacacgc ctacctgaag aacaacaacg tcagcctcta ttacacggcg     660
acatcgttca accgtaatgc tcaggcggt aacatcacac cgccgatcgc catcatctcg     720
cgcgcggatg gacaaattca agcagatgat aagcatgtgt ggttcacggg attcgatcaa     780
catctcccgc tgctcgcacc cgacggcaaa tattatcaga ccggtcagca gaacgagttc     840
ttctccttcc gcgatcccta tgtcttcctt gaccccgctc atccgggcaa gaccttcatg     900
gtcttcgaag gcaataccgc cgtgcagcgc ggctcccgct cctgcaccga ggcagatctc     960
ggatattctc ccaatgaccc gaacaaagaa gacctgaatg cggtcatgga ctccggagcc    1020
atttaccaaa tggccaatgt cggtcttgcc gtggcgacga cgatgaact gacgcagtgg    1080 aagttcctgc cgccgatcct gtccggtaat tgcgtgaacg atcagaccga acgtcctcag    1140
atctatctga aggatggaaa atattacctg ttcacgatca gccaccgcac gacctatgcg    1200
gcgggcgtcg atgggccgga cggcgtctat ggcttcgtcg gtgatggcat tcgcagcgac    1260
ttcattcccc tgaatggcct cagcggtctc acgctcggca acccgaccga tctctatcag    1320
ccggccggcg ctccttacgc cttgaatcca aaccaaaatc ctcggacgtt ccagtcctat    1380
tcgcattatg tcatgccggg cggcctcgtt gaatcgttta tcgatgccat cggccctcgt    1440
cgcggtggcg cgctggctcc gacggtgaag atcaacatca acggaacttc taccatcctc    1500
```

```
gacaggacct atggcaatgc cggattgggt ggctatggcg acatcccggc caatcttccc      1560
gcgcttggcc aagttaatgg ccatggtgtc acgaacggcc agtaa                      1605
```

<210> SEQ ID NO 2
<211> LENGTH: 534
<212> TYPE: PRT
<213> ORGANISM: Beijerinckia indica

<400> SEQUENCE: 2

```
Met Ala Ser Arg Ser Phe Asn Val Cys Ile Arg Ser Leu Ile Ala Gly
1               5                   10                  15

Ser Leu Leu Thr Ala Thr Ala Leu Ser Ala Gln Ala Gln Ser Gly Tyr
            20                  25                  30

Pro Ile Pro Thr Pro His Ser Gly Gln Ala Tyr Asp Pro Phe Ala Asp
        35                  40                  45

Phe Thr Ala Lys Trp Thr Arg Ala Asn Ala Arg Gln Ile Lys Ala Gln
    50                  55                  60

Ser His Val Pro Val Ser Pro Asp Gln Asn Ser Leu Pro Leu Asn Leu
65                  70                  75                  80

Thr Met Pro Asp Ile Pro Ala Asp Phe Pro Gln Thr Asn Pro Asp Val
                85                  90                  95

Trp Val Trp Asp Thr Trp Pro Leu Ala Asp Val His Gly Asn Gln Leu
            100                 105                 110

Ser Phe Gln Gly Trp Glu Val Ile Phe Ser Leu Thr Ala Asp Pro His
        115                 120                 125

Ala Gly Tyr Val Phe Asp Asp Arg His Val His Ala Arg Ile Gly Phe
    130                 135                 140

Phe Tyr Arg Lys Ala Gly Ile Pro Ala Asn Gln Arg Pro Ile Asp Gly
145                 150                 155                 160

Gly Trp Ile Tyr Gly Gly His Leu Phe Pro Asp Gly Ser Ser Val Lys
                165                 170                 175

Val Phe Gly Asn Val Pro Met Thr Gln Asn Ala Glu Trp Ser Gly Gly
            180                 185                 190

Ala Arg Phe Val Gly Gly Pro Tyr Ala Asp Gly Pro Gln His Ala Tyr
        195                 200                 205

Leu Lys Asn Asn Asn Val Ser Leu Tyr Tyr Thr Ala Thr Ser Phe Asn
    210                 215                 220

Arg Asn Ala Gln Gly Gly Asn Ile Thr Pro Pro Ile Ala Ile Ile Ser
225                 230                 235                 240

Arg Ala Asp Gly Gln Ile Gln Ala Asp Lys His Val Trp Phe Thr
                245                 250                 255

Gly Phe Asp Gln His Leu Pro Leu Leu Ala Pro Asp Gly Lys Tyr Tyr
            260                 265                 270

Gln Thr Gly Gln Gln Asn Glu Phe Phe Ser Phe Arg Asp Pro Tyr Val
        275                 280                 285

Phe Leu Asp Pro Ala His Pro Gly Lys Thr Phe Met Val Phe Glu Gly
    290                 295                 300

Asn Thr Ala Val Gln Arg Gly Ser Arg Ser Cys Thr Glu Ala Asp Leu
305                 310                 315                 320

Gly Tyr Ser Pro Asn Asp Pro Asn Lys Glu Asp Leu Asn Ala Val Met
                325                 330                 335

Asp Ser Gly Ala Ile Tyr Gln Met Ala Asn Val Gly Leu Ala Val Ala
            340                 345                 350
```

Thr Asn Asp Glu Leu Thr Gln Trp Lys Phe Leu Pro Pro Ile Leu Ser
            355                 360                 365

Gly Asn Cys Val Asn Asp Gln Thr Glu Arg Pro Gln Ile Tyr Leu Lys
370                 375                 380

Asp Gly Lys Tyr Tyr Leu Phe Thr Ile Ser His Arg Thr Thr Tyr Ala
385                 390                 395                 400

Ala Gly Val Asp Gly Asp Gly Val Tyr Gly Phe Val Gly Asp Gly
            405                 410                 415

Ile Arg Ser Asp Phe Ile Pro Leu Asn Gly Leu Ser Gly Leu Thr Leu
            420                 425                 430

Gly Asn Pro Thr Asp Leu Tyr Gln Pro Ala Gly Ala Pro Tyr Ala Leu
            435                 440                 445

Asn Pro Asn Gln Asn Pro Arg Thr Phe Gln Ser Tyr Ser His Tyr Val
450                 455                 460

Met Pro Gly Gly Leu Val Glu Ser Phe Ile Asp Ala Ile Gly Pro Arg
465                 470                 475                 480

Arg Gly Gly Ala Leu Ala Pro Thr Val Lys Ile Asn Ile Asn Gly Thr
            485                 490                 495

Ser Thr Ile Leu Asp Arg Thr Tyr Gly Asn Ala Gly Leu Gly Gly Tyr
            500                 505                 510

Gly Asp Ile Pro Ala Asn Leu Pro Ala Leu Gly Gln Val Asn Gly His
            515                 520                 525

Gly Val Thr Asn Gly Gln
            530

<210> SEQ ID NO 3
<211> LENGTH: 31
<212> TYPE: DNA
<213> ORGANISM: Artificial Sequence
<220> FEATURE:
<223> OTHER INFORMATION: forward primer

<400> SEQUENCE: 3
atggcaagtc gatcgtttaa tgtttgtata c                                  31

<210> SEQ ID NO 4
<211> LENGTH: 33
<212> TYPE: DNA
<213> ORGANISM: Artificial Sequence
<220> FEATURE:
<223> OTHER INFORMATION: reverse primer

<400> SEQUENCE: 4
tttaccagac tcgagttact ggccgttcgt gac                                33

<210> SEQ ID NO 5
<211> LENGTH: 59
<212> TYPE: DNA
<213> ORGANISM: Artificial Sequence
<220> FEATURE:
<223> OTHER INFORMATION: forward primer

<400> SEQUENCE: 5
ccgcgcggca gccatggtta cccgataccg actccgcatt cgggacaagc ctatgatcc    59

<210> SEQ ID NO 6
<211> LENGTH: 68
<212> TYPE: DNA
<213> ORGANISM: Artificial Sequence
<220> FEATURE:
<223> OTHER INFORMATION: reverse primer

<400> SEQUENCE: 6

```
gtggtggtgc tcgagttact ggccgttcgt gacaccatgg ccattacctt ggccaagcgc    60
gggaagat                                                             68
```

<210> SEQ ID NO 7
<211> LENGTH: 27
<212> TYPE: DNA
<213> ORGANISM: Artificial Sequence
<220> FEATURE:
<223> OTHER INFORMATION: forward primer

<400> SEQUENCE: 7

```
ctcgagcacc accaccacca ccactga                                        27
```

<210> SEQ ID NO 8
<211> LENGTH: 27
<212> TYPE: DNA
<213> ORGANISM: Artificial Sequence
<220> FEATURE:
<223> OTHER INFORMATION: reverse primer

<400> SEQUENCE: 8

```
atggctgccg cgcggcacca ggccgct                                        27
```

<210> SEQ ID NO 9
<211> LENGTH: 31
<212> TYPE: DNA
<213> ORGANISM: Artificial Sequence
<220> FEATURE:
<223> OTHER INFORMATION: forward primer

<400> SEQUENCE: 9

```
aaacatatga aaaagaact gagctttcat g                                    31
```

<210> SEQ ID NO 10
<211> LENGTH: 33
<212> TYPE: DNA
<213> ORGANISM: Artificial Sequence
<220> FEATURE:
<223> OTHER INFORMATION: reverse primer

<400> SEQUENCE: 10

```
aaaagatctt ttagatttta gtttgtcact atg                                 33
```

<210> SEQ ID NO 11
<211> LENGTH: 1143
<212> TYPE: DNA
<213> ORGANISM: Bacillus subtilis

<400> SEQUENCE: 11

```
atgaaaaaag aactgagctt tcatgaaaag ctgctaaagc tgacaaaaca gcaaaaaaag    60
aaaaccaata agcacgtatt tattgccatt ccgatcgttt ttgtccttat gttcgctttc   120
atgtgggcgg aaaagcgga aacgccgaag gtcaaaacgt attctgacga cgtactctca   180
gcctcatttg taggcgatat tatgatggga cgctatgttg aaaaagtaac ggagcaaaaa   240
ggggcagaca gtatttttca atatgttgaa ccgatcttta gagcctcgga ttatgtagca   300
ggaaactttg aaacccggt aacctatcaa agaattata acaagcaga taagagatt     360 catctgcaga cgaataagga atcagtgaaa gtcttgaagg atatgaattt cacggttctc   420
aacagcgcca acaccacgc aatggattac ggcgttcagg gcatgaaaga tacgcttgga   480
gaatttgcga agcaaaatct tgatatcgtt ggagcgggat acagcttaag tgatgcgaaa   540
```

-continued

```
aagaaaattt cgtaccagaa agtcaacggg gtaacgattg cgacgcttgg ctttaccgat    600
gtgtccggga aaggtttcgc ggctaaaaag aatacgccgg gcgtgctgcc cgcagatcct    660
gaaatcttca tccctatgat ttcagaagcg aaaaaacatg cggacattgt tgttgtgcag    720
tcacactggg gacaagagta tgacaatgat ccaaatgacc gccagcgcca gcttgcaaga    780
gccatgtctg atgcgggagc tgacatcatc gtcggccatc acccgcacgt cttagaaccg    840
attgaagtat ataacggaac cgtcattttc tacagcctcg gcaactttgt ctttgaccaa    900
ggctggacga gaacaagaga cagtgcactg gttcagtatc acctgaagaa aaatggaaca    960
ggacgctttg aagtgacacc gatcgatatc catgaagcga cacctgcgcc tgtgaaaaaa   1020
gacagcctta aacagaaaac cattattcgc gaactgacga aagactctaa tttcgcttgg   1080
aaagtagaag acggaaaact gacgtttgat attgatcata gtgacaaact aaaatctaaa   1140
taa                                                                 1143
```

<210> SEQ ID NO 12
<211> LENGTH: 380
<212> TYPE: PRT
<213> ORGANISM: Bacillus subtilis

<400> SEQUENCE: 12

```
Met Lys Lys Glu Leu Ser Phe His Glu Lys Leu Leu Lys Leu Thr Lys
1               5                   10                  15

Gln Gln Lys Lys Lys Thr Asn Lys His Val Phe Ile Ala Ile Pro Ile
            20                  25                  30

Val Phe Val Leu Met Phe Ala Phe Met Trp Ala Gly Lys Ala Glu Thr
        35                  40                  45

Pro Lys Val Lys Thr Tyr Ser Asp Asp Val Leu Ser Ala Ser Phe Val
    50                  55                  60

Gly Asp Ile Met Met Gly Arg Tyr Val Glu Lys Val Thr Glu Gln Lys
65                  70                  75                  80

Gly Ala Asp Ser Ile Phe Gln Tyr Val Glu Pro Ile Phe Arg Ala Ser
                85                  90                  95

Asp Tyr Val Ala Gly Asn Phe Glu Asn Pro Val Thr Tyr Gln Lys Asn
            100                 105                 110

Tyr Lys Gln Ala Asp Lys Glu Ile His Leu Gln Thr Asn Lys Glu Ser
        115                 120                 125

Val Lys Val Leu Lys Asp Met Asn Phe Thr Val Leu Asn Ser Ala Asn
    130                 135                 140

Asn His Ala Met Asp Tyr Gly Val Gln Gly Met Lys Asp Thr Leu Gly
145                 150                 155                 160

Glu Phe Ala Lys Gln Asn Leu Asp Ile Val Gly Ala Gly Tyr Ser Leu
                165                 170                 175

Ser Asp Ala Lys Lys Ile Ser Tyr Gln Lys Val Asn Gly Val Thr
            180                 185                 190

Ile Ala Thr Leu Gly Phe Thr Asp Val Ser Gly Lys Gly Phe Ala Ala
        195                 200                 205

Lys Lys Asn Thr Pro Gly Val Leu Pro Ala Asp Pro Glu Ile Phe Ile
    210                 215                 220

Pro Met Ile Ser Glu Ala Lys Lys His Ala Asp Ile Val Val Val Gln
225                 230                 235                 240

Ser His Trp Gly Gln Glu Tyr Asp Asn Asp Pro Asn Asp Arg Gln Arg
                245                 250                 255
```

```
Gln Leu Ala Arg Ala Met Ser Asp Ala Gly Ala Asp Ile Ile Val Gly
            260                 265                 270

His His Pro His Val Leu Glu Pro Ile Glu Val Tyr Asn Gly Thr Val
            275                 280                 285

Ile Phe Tyr Ser Leu Gly Asn Phe Val Phe Asp Gln Gly Trp Thr Arg
            290                 295                 300

Thr Arg Asp Ser Ala Leu Val Gln Tyr His Leu Lys Lys Asn Gly Thr
305                 310                 315                 320

Gly Arg Phe Glu Val Thr Pro Ile Asp Ile His Glu Ala Thr Pro Ala
                325                 330                 335

Pro Val Lys Lys Asp Ser Leu Lys Gln Lys Thr Ile Ile Arg Glu Leu
            340                 345                 350

Thr Lys Asp Ser Asn Phe Ala Trp Lys Val Glu Asp Gly Lys Leu Thr
            355                 360                 365

Phe Asp Ile Asp His Ser Asp Lys Leu Lys Ser Lys
            370                 375                 380

<210> SEQ ID NO 13
<211> LENGTH: 44
<212> TYPE: DNA
<213> ORGANISM: Artificial Sequence
<220> FEATURE:
<223> OTHER INFORMATION: forward primer

<400> SEQUENCE: 13
aaaggatcct cgggttaccc gataccgact ccgcattcgg gaca                44

<210> SEQ ID NO 14
<211> LENGTH: 42
<212> TYPE: DNA
<213> ORGANISM: Artificial Sequence
<220> FEATURE:
<223> OTHER INFORMATION: reverse primer

<400> SEQUENCE: 14
cccctcgagt tactggccgt tcgtgacacc atggccatta ac                  42

<210> SEQ ID NO 15
<211> LENGTH: 1197
<212> TYPE: DNA
<213> ORGANISM: Artificial Sequence
<220> FEATURE:
<223> OTHER INFORMATION: capA_opti gene

<400> SEQUENCE: 15
atgaaagaaa agaaactgaa cttccaagaa aaggtcctga tgtttattaa gaaaaccaag    60
ccgacgacgg gcaagcaagc actgattctg acgccgatcc tgattgttat cctggctctg   120
tcgggctgga tggaacgtag cgatgcgctg aaaaacccgg aaaccgccaa tccggaagca   180
aacaatgatc tgaccatgac gatggtgggc gacattatga tgggtcgtca tgtgcgcgaa   240
gttaccgaac gttatggcga agattttgtc ttccgcaacg tggaaccgtt tttcaaaaat   300
agcgactatg tgtctggtaa ctacgaaacg ccgattctga ccaatgatgt tgactcctat   360
aaagcgatgg aaaagggcat ccatctgtac tcaaaaccgg ctgatctggc gaccgtgaag   420
aatgctggtt ttgacgttct gaacctggcg aacaatcaca gtatggatta tccgctaaa   480 ggcctggaag acacgattag cacctttgaa gcaaataagc tggatttcgt gggcgctggt   540
cgtaactctg aagaagcgaa acatatcagt tacaaggatg ccgacggcat tcgcatcgca   600
acggttggtt ttaccgatgt ccactcagac ggcatgtcgg ccggtaaaaa caatccgggt   660
```

-continued

```
attctgaagg cagatccgga cctgattttc tcgaccatcc agcaagcaaa agctaatgcg   720
gatctggtgg ttgtcaacgc ccattggggc gaagaatatg acgcacagcc gagtccgcgc   780
caagaaggtc tggccaaagc aatggtcgat gctggcgcgg acattatcat tggtcatcac   840
ccgcacgtgc tgcagagcta tgatgtgtac aaaggtagcg ttatctttta ttctctgggc   900
aacttcatct tcgatcaggg ttggagctct acgaagaata ccgccatggt gcaataccat   960
ctgaacaaac agggccaagc taagattgat gttatcccga tggtcattaa agcgggtacc  1020
ccgacgccga ccgataatcc gtggcgtatg aaacgcatct ataacgacct gaataagttt  1080
agttccaacc cggaactgct ggaaaaagaa cgtaacaagt cgaactgaa tctggatcat   1140 tcccgtatca ttaaacacgc ggaagaacgc aaaaagaacg aagcccaggc aaattaa    1197
```

<210> SEQ ID NO 16
<211> LENGTH: 400
<212> TYPE: PRT
<213> ORGANISM: Artificial Sequence
<220> FEATURE:
<223> OTHER INFORMATION: capA_opti gene amino acid sequence

<400> SEQUENCE: 16

```
Met Lys Glu Lys Lys Leu Asn Phe Gln Glu Lys Val Leu Met Phe Ile
1               5                   10                  15

Lys Lys Thr Lys Pro Thr Thr Gly Lys Gln Ala Leu Ile Leu Thr Pro
                20                  25                  30

Ile Leu Ile Val Ile Leu Ala Leu Ser Gly Trp Met Glu Arg Ser Asp
            35                  40                  45

Ala Leu Glu Asn Pro Glu Thr Ala Asn Pro Glu Asn Asn Asp Leu
        50                  55                  60

Thr Met Thr Met Val Gly Asp Ile Met Met Gly Arg His Val Arg Glu
65                  70                  75                  80

Val Thr Glu Arg Tyr Gly Glu Asp Phe Val Phe Arg Asn Val Glu Pro
                85                  90                  95

Phe Phe Lys Asn Ser Asp Tyr Val Ser Gly Asn Tyr Glu Thr Pro Ile
                100                 105                 110

Leu Thr Asn Asp Val Asp Ser Tyr Lys Ala Met Glu Lys Gly Ile His
            115                 120                 125

Leu Tyr Ser Lys Pro Ala Asp Leu Ala Thr Val Lys Asn Ala Gly Phe
        130                 135                 140

Asp Val Leu Asn Leu Ala Asn Asn His Ser Met Asp Tyr Ser Ala Lys
145                 150                 155                 160

Gly Leu Glu Asp Thr Ile Ser Thr Phe Glu Ala Asn Lys Leu Asp Phe
                165                 170                 175

Val Gly Ala Gly Arg Asn Ser Glu Glu Ala Lys His Ile Ser Tyr Lys
                180                 185                 190

Asp Ala Asp Gly Ile Arg Ile Ala Thr Val Gly Phe Thr Asp Val His
            195                 200                 205

Ser Asp Gly Met Ser Ala Gly Lys Asn Asn Pro Gly Ile Leu Lys Ala
        210                 215                 220

Asp Pro Asp Leu Ile Phe Ser Thr Ile Gln Gln Ala Lys Ala Asn Ala
225                 230                 235                 240

Asp Leu Val Val Val Asn Ala His Trp Gly Glu Glu Tyr Asp Ala Gln
                245                 250                 255

Pro Ser Pro Arg Gln Glu Gly Leu Ala Lys Ala Met Val Asp Ala Gly
                260                 265                 270
```

```
Ala Asp Ile Ile Ile Gly His His Pro His Val Leu Gln Ser Tyr Asp
            275                 280                 285

Val Tyr Lys Gly Ser Val Ile Phe Tyr Ser Leu Gly Asn Phe Ile Phe
            290                 295                 300

Asp Gln Gly Trp Ser Ser Thr Lys Asn Thr Ala Met Val Gln Tyr His
305                 310                 315                 320

Leu Asn Lys Gln Gly Gln Ala Lys Ile Asp Val Ile Pro Met Val Ile
            325                 330                 335

Lys Ala Gly Thr Pro Thr Pro Thr Asp Asn Pro Trp Arg Met Lys Arg
            340                 345                 350

Ile Tyr Asn Asp Leu Asn Lys Phe Ser Ser Asn Pro Glu Leu Leu Glu
            355                 360                 365

Lys Glu Arg Asn Lys Phe Glu Leu Asn Leu Asp His Ser Arg Ile Ile
            370                 375                 380

Lys His Ala Glu Glu Arg Lys Lys Asn Glu Ala Gln Ala Asn Arg Ser
385                 390                 395                 400

<210> SEQ ID NO 17
<211> LENGTH: 46
<212> TYPE: DNA
<213> ORGANISM: Artificial Sequence
<220> FEATURE:
<223> OTHER INFORMATION: forward primer

<400> SEQUENCE: 17
taagaaggag atatacatat gaaagaaaag aaactgaact tccaag                46

<210> SEQ ID NO 18
<211> LENGTH: 46
<212> TYPE: DNA
<213> ORGANISM: Artificial Sequence
<220> FEATURE:
<223> OTHER INFORMATION: reverse primer

<400> SEQUENCE: 18
cgggtaaccc gattgagatc tatttgcctg ggcttcgttc tttttg                46

<210> SEQ ID NO 19
<211> LENGTH: 29
<212> TYPE: DNA
<213> ORGANISM: Artificial Sequence
<220> FEATURE:
<223> OTHER INFORMATION: forward primer

<400> SEQUENCE: 19
agatctcaat cgggttaccc gataccgac                                   29

<210> SEQ ID NO 20
<211> LENGTH: 29
<212> TYPE: DNA
<213> ORGANISM: Artificial Sequence
<220> FEATURE:
<223> OTHER INFORMATION: reverse primer

<400> SEQUENCE: 20
catatgtata tctccttctt atacttaac                                   29

<210> SEQ ID NO 21
<211> LENGTH: 29
<212> TYPE: DNA
<213> ORGANISM: Artificial Sequence
<220> FEATURE:
<223> OTHER INFORMATION: forward primer
```

```
<400> SEQUENCE: 21
tgtaccgctg atccgcatgc cggttatgt                                        29

<210> SEQ ID NO 22
<211> LENGTH: 30
<212> TYPE: DNA
<213> ORGANISM: Artificial Sequence
<220> FEATURE:
<223> OTHER INFORMATION: reverse primer

<400> SEQUENCE: 22
cgagaaaatg acctcccacc cctggaagct                                       30

<210> SEQ ID NO 23
<211> LENGTH: 30
<212> TYPE: DNA
<213> ORGANISM: Artificial Sequence
<220> FEATURE:
<223> OTHER INFORMATION: forward primer

<400> SEQUENCE: 23
cgtcgcacga cctatgcggc gggcgtcgat                                       30

<210> SEQ ID NO 24
<211> LENGTH: 30
<212> TYPE: DNA
<213> ORGANISM: Artificial Sequence
<220> FEATURE:
<223> OTHER INFORMATION: reverse primer

<400> SEQUENCE: 24
gctgatcgtg aacaggtaat attttccatc                                       30

<210> SEQ ID NO 25
<211> LENGTH: 30
<212> TYPE: DNA
<213> ORGANISM: Artificial Sequence
<220> FEATURE:
<223> OTHER INFORMATION: forward primer

<400> SEQUENCE: 25
aaacgcacga cctatgcggc gggcgtcgat                                       30

<210> SEQ ID NO 26
<211> LENGTH: 30
<212> TYPE: DNA
<213> ORGANISM: Artificial Sequence
<220> FEATURE:
<223> OTHER INFORMATION: reverse primer

<400> SEQUENCE: 26
gctgatcgtg aacaggtaat attttccatc                                       30

<210> SEQ ID NO 27
<211> LENGTH: 30
<212> TYPE: DNA
<213> ORGANISM: Artificial Sequence
<220> FEATURE:
<223> OTHER INFORMATION: forward primer

<400> SEQUENCE: 27
tatatcgatg ccatcggccc tcgtcgcggt                                       30
```

```
<210> SEQ ID NO 28
<211> LENGTH: 30
<212> TYPE: DNA
<213> ORGANISM: Artificial Sequence
<220> FEATURE:
<223> OTHER INFORMATION: reverse primer

<400> SEQUENCE: 28
cgattcaacg aggccgcccg gcatgacata                                   30

<210> SEQ ID NO 29
<211> LENGTH: 29
<212> TYPE: DNA
<213> ORGANISM: Artificial Sequence
<220> FEATURE:
<223> OTHER INFORMATION: forward primer

<400> SEQUENCE: 29
tgtaccgctg atccgcatgc cggttatgt                                    29

<210> SEQ ID NO 30
<211> LENGTH: 30
<212> TYPE: DNA
<213> ORGANISM: Artificial Sequence
<220> FEATURE:
<223> OTHER INFORMATION: reverse primer

<400> SEQUENCE: 30
cgagaaaatg acctcccacc cctggaagct                                   30

<210> SEQ ID NO 31
<211> LENGTH: 30
<212> TYPE: DNA
<213> ORGANISM: Artificial Sequence
<220> FEATURE:
<223> OTHER INFORMATION: forward primer

<400> SEQUENCE: 31
tatatcgatg ccatcggccc tcgtcgcggt                                   30

<210> SEQ ID NO 32
<211> LENGTH: 30
<212> TYPE: DNA
<213> ORGANISM: Artificial Sequence
<220> FEATURE:
<223> OTHER INFORMATION: reverse primer

<400> SEQUENCE: 32
cgattcaacg aggccgcccg gcatgacata                                   30

<210> SEQ ID NO 33
<211> LENGTH: 29
<212> TYPE: DNA
<213> ORGANISM: Artificial Sequence
<220> FEATURE:
<223> OTHER INFORMATION: forward primer

<400> SEQUENCE: 33
tgtaccgctg atccgcatgc cggttatgt                                    29

<210> SEQ ID NO 34
<211> LENGTH: 30
<212> TYPE: DNA
<213> ORGANISM: Artificial Sequence
<220> FEATURE:
<223> OTHER INFORMATION: reverse primer
```

<400> SEQUENCE: 34
cgagaaaatg acctcccacc cctggaagct         30

<210> SEQ ID NO 35
<211> LENGTH: 29
<212> TYPE: DNA
<213> ORGANISM: Artificial Sequence
<220> FEATURE:
<223> OTHER INFORMATION: forward primer

<400> SEQUENCE: 35
tgtaccgctg atccgcatgc cggttatgt          29

<210> SEQ ID NO 36
<211> LENGTH: 30
<212> TYPE: DNA
<213> ORGANISM: Artificial Sequence
<220> FEATURE:
<223> OTHER INFORMATION: reverse primer

<400> SEQUENCE: 36
cgagaaaatg acctcccacc cctggaagct         30

<210> SEQ ID NO 37
<211> LENGTH: 1596
<212> TYPE: DNA
<213> ORGANISM: Burkholderia phymatum STM815

<400> SEQUENCE: 37
atgaacgttg gccaccaccc gcgggtcccc cggatcaccc cccggctgcg cgcgcacttc    60
ctgtcggcag cggtgctgtc ggctgttgcc ctaccggcgc tggctcagac tgcaacgcca   120
ggcttccccg cgccgacgcc gcactcgcag caggcatacg accccgagag cagtttcacg   180
atgcgctgga cccgtgccga catccgtcag atcaaggcgc agtcgcatgc cgcgacggcg   240
gcggacaaga actcgctgcc gctttcgctg accatgccgg acatcccgca ggatttcccg   300
ctgatcaatc cgaacgtctg ggtgtgggac acgtggccgc tggccgacat gcgggcgaac   360
cagctggcgt acaagggctg ggaggtgatc ttttcgctga cggccgatcc gcatgccggc   420
tatacgttcg acgaccgtca cgttcacgcg cgcatcggct tcttctaccg ccgcgcgggc   480
attcccgcat cgcagcgacc cgcgaacggc ggctggacct ggggcggcca tctgttcccg   540
gacggtgcga gcgtcaaggt attcggcacg tcgccgatga ccgacaacgc cgaatggtcg   600
ggctcggcgc gtctcacgca cggcgacaac gtcagcctct actacaccgc gacgtcgttc   660
aaccgttcgg ccccgccggcgg cgccgacatt acgccgccgc aggcgatcat cacgcgcgcc   720
gacggtcaca tccacgccga cgacagtcat gtgtggttct caggcttcga cgatcaccag   780
gcattgctca agccggacgg cacctactac cagaccggcg agcagaacac ctacttctca   840
taccgggatc cgttcgtgtt catcgatccc gcgcatccag gcaagaccta catggtgttc   900
gaaggcaaca cgggcggtcc gcgcggcgcg cgcacctgta cggaagccga cctcggctat   960
gcgccgaacg atccgcaacg ggaagacctg aacgcggtga tgaactcggg cgcggcgtat  1020
cagaaggcca atgttggtct cgcggtcgcg acgaatccgc aactgaccga atggaagttc  1080
ctgccaccga tcctgtcggc gaactgcgtc gatgatcaga ccgagcgccc gcagatttac  1140
ctgaaggacg gcaagtacta cctgttcacg atcagccacc gcacaacgat ggcagcaggc  1200
gttgacggac cggacggtgt ctacggcttc gtcggcaacg gcatccgcag cgacttcttg  1260
ccgctgaacg gcggcagcgg cctcgtactc ggcaacccga ccgacttttc cgccccggcg  1320

```
ggtgcgccgt acgcgcagga cccgaaccag aacccgcgcg agttccagtc gtactcgcac    1380
tacgtgatgc cgggtggtct cgtcgagtcg tttatcgatg caatcggctc gcggcgcggc    1440
ggcacgcttg cgccgaccgt caagatcaac atcaacggtg acacgacggt cgtggaccgg    1500
acgtatggca aggcggtct cggcggctac ggcgacattc ccgcaaacca gtcggcgccc     1560
ggcaatggaa acgggcaggg cggcaacagc cagtaa                              1596
```

<210> SEQ ID NO 38
<211> LENGTH: 531
<212> TYPE: PRT
<213> ORGANISM: Burkholderia phymatum STM815

<400> SEQUENCE: 38

```
Met Asn Val Gly His His Pro Arg Val Pro Arg Ile Thr Pro Arg Leu
1               5                   10                  15

Arg Ala His Phe Leu Ser Ala Ala Val Leu Ser Ala Val Ala Leu Pro
            20                  25                  30

Ala Leu Ala Gln Thr Ala Thr Pro Gly Phe Pro Ala Pro Thr Pro His
        35                  40                  45

Ser Gln Gln Ala Tyr Asp Pro Glu Ser Ser Phe Thr Met Arg Trp Thr
    50                  55                  60

Arg Ala Asp Ile Arg Gln Ile Lys Ala Gln Ser His Ala Ala Thr Ala
65                  70                  75                  80

Ala Asp Lys Asn Ser Leu Pro Leu Ser Leu Thr Met Pro Asp Ile Pro
                85                  90                  95

Gln Asp Phe Pro Leu Ile Asn Pro Asn Val Trp Val Trp Asp Thr Trp
            100                 105                 110

Pro Leu Ala Asp Met Arg Ala Asn Gln Leu Ala Tyr Lys Gly Trp Glu
        115                 120                 125

Val Ile Phe Ser Leu Thr Ala Asp Pro His Ala Gly Tyr Thr Phe Asp
    130                 135                 140

Asp Arg His Val His Ala Arg Ile Gly Phe Phe Tyr Arg Arg Ala Gly
145                 150                 155                 160

Ile Pro Ala Ser Gln Arg Pro Asn Gly Gly Trp Thr Trp Gly Gly
                165                 170                 175

His Leu Phe Pro Asp Gly Ala Ser Val Lys Val Phe Gly Thr Ser Pro
            180                 185                 190

Met Thr Asp Asn Ala Glu Trp Ser Gly Ser Ala Arg Leu Thr His Gly
        195                 200                 205

Asp Asn Val Ser Leu Tyr Tyr Thr Ala Thr Ser Phe Asn Arg Ser Ala
    210                 215                 220

Pro Gly Gly Ala Asp Ile Thr Pro Pro Gln Ala Ile Ile Thr Arg Ala
225                 230                 235                 240

Asp Gly His Ile His Ala Asp Asp Ser His Val Trp Phe Ser Gly Phe
                245                 250                 255

Asp Asp His Gln Ala Leu Leu Lys Pro Asp Gly Thr Tyr Tyr Gln Thr
            260                 265                 270

Gly Glu Gln Asn Thr Tyr Phe Ser Tyr Arg Asp Pro Phe Val Phe Ile
        275                 280                 285

Asp Pro Ala His Pro Gly Lys Thr Tyr Met Val Phe Glu Gly Asn Thr
    290                 295                 300

Gly Gly Pro Arg Gly Ala Arg Thr Cys Thr Glu Ala Asp Leu Gly Tyr
305                 310                 315                 320
```

```
Ala Pro Asn Asp Pro Gln Arg Glu Asp Leu Asn Ala Val Met Asn Ser
                325                 330                 335

Gly Ala Ala Tyr Gln Lys Ala Asn Val Gly Leu Ala Val Ala Thr Asn
            340                 345                 350

Pro Gln Leu Thr Glu Trp Lys Phe Leu Pro Pro Ile Leu Ser Ala Asn
        355                 360                 365

Cys Val Asp Asp Gln Thr Glu Arg Pro Gln Ile Tyr Leu Lys Asp Gly
370                 375                 380

Lys Tyr Tyr Leu Phe Thr Ile Ser His Arg Thr Met Ala Ala Gly
385                 390                 395                 400

Val Asp Gly Pro Asp Gly Val Tyr Gly Phe Val Gly Asn Gly Ile Arg
                405                 410                 415

Ser Asp Phe Leu Pro Leu Asn Gly Gly Ser Gly Leu Val Leu Gly Asn
            420                 425                 430

Pro Thr Asp Phe Ser Ala Pro Ala Gly Ala Pro Tyr Ala Gln Asp Pro
        435                 440                 445

Asn Gln Asn Pro Arg Glu Phe Gln Ser Tyr Ser His Tyr Val Met Pro
450                 455                 460

Gly Gly Leu Val Glu Ser Phe Ile Asp Ala Ile Gly Ser Arg Arg Gly
465                 470                 475                 480

Gly Thr Leu Ala Pro Thr Val Lys Ile Asn Ile Asn Gly Asp Thr Thr
                485                 490                 495

Val Val Asp Arg Thr Tyr Gly Lys Gly Gly Leu Gly Gly Tyr Gly Asp
            500                 505                 510

Ile Pro Ala Asn Gln Ser Ala Pro Gly Asn Gly Asn Gly Gln Gly Gly
        515                 520                 525

Asn Ser Gln
    530
```

<210> SEQ ID NO 39
<211> LENGTH: 46
<212> TYPE: DNA
<213> ORGANISM: Artificial Sequence
<220> FEATURE:
<223> OTHER INFORMATION: forward primer

<400> SEQUENCE: 39
aaactaaaat ctaaaagatc tcagactgca acgccaggct tccccg          46

<210> SEQ ID NO 40
<211> LENGTH: 51
<212> TYPE: DNA
<213> ORGANISM: Artificial Sequence
<220> FEATURE:
<223> OTHER INFORMATION: reverse primer

<400> SEQUENCE: 40
ggtttcttta ccagactcga gttactggct gttgccgccc tgcccgtttc c       51

<210> SEQ ID NO 41
<211> LENGTH: 1755
<212> TYPE: DNA
<213> ORGANISM: Artificial Sequence
<220> FEATURE:
<223> OTHER INFORMATION: glucono_opti gene

<400> SEQUENCE: 41
atggctcacg tccgtcgtaa agtcgcaacg ctgaacatgg ctctggcggg tagtctgctg    60
atggtcctgg gtgcccaatc tgctctggcc caaggcaatt tttctcgcca ggaagcggca   120

-continued

```
cgtatggcac atcgtccggg tgttatgccg cgtggcggtc cgctgtttcc gggtcgcagc    180
ctggccggtg tgccgggttt cccgctgccg tctattcata cccagcaagc atatgatccg    240
cagagtgact ttaccgctcg ttggacccgt gccgatgcac tgcagatcaa agcgcactca    300
gacgccaccg ttgcagctgg ccaaaactcg ctgccggcgc agctgacgat gccgaatatt    360
ccggccgatt tcccggtcat caacccggat gtttgggttt gggacacctg gacgctgatt    420
gataagcacg cggaccagtt tagctataat ggttgggaag tgatcttctg cctgaccgca    480
gatccgaacg ctggctatgg ttttgatgac cgtcatgttc acgcccgcat ggcttttttc    540
taccgtcgcg ccggtattcc ggcaagccgt cgcccggtca atggcggttg gacgtatggc    600
ggtcacctgt ttccggatgg cgcaagcgcg caggtgtatg caggtcaaac ctacacgaat    660
caggctgaat ggtccggcag ctctcgtctg atgcagattc acgtaacac cgtctcagtg     720
ttttacacgg atgtggcgtt caaccgcgac gcgaatgcca acaatattac cccgccgcaa    780
gcaattatca cccagacgct gggccgtatc catgctgatt taaccacgt ttggtttacc     840
ggtttcacgg cacataccc gctgctgcag ccggatggcg tcctgtatca gaacggtgcg     900
caaaatgaat ttttcaactt cgtgatccg tttaccttcg aagacccgaa cacccgggc      960
gtgaattaca tggttttcga gggtaacacc gccggccagc gtggtgtggc aaattgcacg    1020
gaagctgatc tgggctttcg cccgaacgac ccgaatgcag aaaccctgca agaagttctg    1080
gatagcggcg cgtattacca gaaagccaac attggtctgg caatcgctac ggactcaacc    1140
ctgtcgaaat ggaagtttct gagcccgctg atttctgcga actgcgtgaa tgatcaaacc    1200
gaacgtccgc aggtttacct gcataacggc aagtactaca tcttcacgat cagccatcgc    1260
accaccttg cggcgggtgt ggatggtccg gatggcgtct atggttttgt gggcgatggt     1320
atccgcagtg acttccagcc gatgaactac ggctccggtc tgaccatggg caatccgacg    1380
gatctgaaca ccgcagctgg tacgattttt gacccgtctc cggaccaaaa tccgcgtgcc    1440
ttccagagtt attcccatta cgttatgccg ggcggtctgg tcgaaagttt tattgatacc    1500
gttgaaaatc gtcgcggcgg taccctggcc ccgacggttc gtgtccgcat cgcccagaat    1560
gcgtccgccg tggatctgcg ttatggcaac ggcggtctgg gcggttacgg tgatattccg    1620
gcaaatcgcg ctgatgtgaa cattgcgggt tttatccaag acctgtttgg ccagccgacc    1680
agtggtctgg ccgctcaagc aagcacgaat aacgctcaag ttctggcaca ggtccgtcaa    1740
tttctgaatc aataa                                                     1755
```

<210> SEQ ID NO 42
<211> LENGTH: 584
<212> TYPE: PRT
<213> ORGANISM: Artificial Sequence
<220> FEATURE:
<223> OTHER INFORMATION: glucono_opti gene amino acid sequence

<400> SEQUENCE: 42

```
Met Ala His Val Arg Arg Lys Val Ala Thr Leu Asn Met Ala Leu Ala
1               5                   10                  15

Gly Ser Leu Leu Met Val Leu Gly Ala Gln Ser Ala Leu Ala Gln Gly
            20                  25                  30

Asn Phe Ser Arg Gln Glu Ala Ala Arg Met Ala His Arg Pro Gly Val
        35                  40                  45

Met Pro Arg Gly Gly Pro Leu Phe Pro Gly Arg Ser Leu Ala Gly Val
    50                  55                  60
```

```
Pro Gly Phe Pro Leu Pro Ser Ile His Thr Gln Ala Tyr Asp Pro
 65                  70                  75                  80

Gln Ser Asp Phe Thr Ala Arg Trp Thr Arg Ala Asp Ala Leu Gln Ile
                 85                  90                  95

Lys Ala His Ser Asp Ala Thr Val Ala Ala Gly Gln Asn Ser Leu Pro
            100                 105                 110

Ala Gln Leu Thr Met Pro Asn Ile Pro Ala Asp Phe Pro Val Ile Asn
        115                 120                 125

Pro Asp Val Trp Val Trp Asp Thr Trp Thr Leu Ile Asp Lys His Ala
130                 135                 140

Asp Gln Phe Ser Tyr Asn Gly Trp Glu Val Ile Phe Cys Leu Thr Ala
145                 150                 155                 160

Asp Pro Asn Ala Gly Tyr Gly Phe Asp Arg His Val His Ala Arg
                165                 170                 175

Ile Gly Phe Phe Tyr Arg Arg Ala Gly Ile Pro Ala Ser Arg Arg Pro
                180                 185                 190

Val Asn Gly Gly Trp Thr Tyr Gly Gly His Leu Phe Pro Asp Gly Ala
                195                 200                 205

Ser Ala Gln Val Tyr Ala Gly Gln Thr Tyr Thr Asn Gln Ala Glu Trp
            210                 215                 220

Ser Gly Ser Ser Arg Leu Met Gln Ile His Gly Asn Thr Val Ser Val
225                 230                 235                 240

Phe Tyr Thr Asp Val Ala Phe Asn Arg Asp Ala Asn Ala Asn Asn Ile
                245                 250                 255

Thr Pro Pro Gln Ala Ile Ile Thr Gln Thr Leu Gly Arg Ile His Ala
            260                 265                 270

Asp Phe Asn His Val Trp Phe Thr Gly Phe Thr Ala His Thr Pro Leu
            275                 280                 285

Leu Gln Pro Asp Gly Val Leu Tyr Gln Asn Gly Ala Gln Asn Glu Phe
        290                 295                 300

Phe Asn Phe Arg Asp Pro Phe Thr Phe Glu Asp Pro Lys His Pro Gly
305                 310                 315                 320

Val Asn Tyr Met Val Phe Glu Gly Asn Thr Ala Gly Gln Arg Gly Val
                325                 330                 335

Ala Asn Cys Thr Glu Ala Asp Leu Gly Phe Arg Pro Asn Asp Pro Asn
            340                 345                 350

Ala Glu Thr Leu Gln Glu Val Leu Asp Ser Gly Ala Tyr Tyr Gln Lys
            355                 360                 365

Ala Asn Ile Gly Leu Ala Ile Ala Thr Asp Ser Thr Leu Ser Lys Trp
        370                 375                 380

Lys Phe Leu Ser Pro Leu Ile Ser Ala Asn Cys Val Asn Asp Gln Thr
385                 390                 395                 400

Glu Arg Pro Gln Val Tyr Leu His Asn Gly Lys Tyr Tyr Ile Phe Thr
                405                 410                 415

Ile Ser His Arg Thr Thr Phe Ala Ala Gly Val Asp Gly Pro Asp Gly
            420                 425                 430

Val Tyr Gly Phe Val Gly Asp Gly Ile Arg Ser Asp Phe Gln Pro Met
        435                 440                 445

Asn Tyr Gly Ser Gly Leu Thr Met Gly Asn Pro Thr Asp Leu Asn Thr
        450                 455                 460

Ala Ala Gly Thr Asp Phe Asp Pro Ser Pro Asp Gln Asn Pro Arg Ala
465                 470                 475                 480
```

Phe Gln Ser Tyr Ser His Tyr Val Met Pro Gly Gly Leu Val Glu Ser
                485                 490                 495

Phe Ile Asp Thr Val Glu Asn Arg Arg Gly Gly Thr Leu Ala Pro Thr
            500                 505                 510

Val Arg Val Arg Ile Ala Gln Asn Ala Ser Ala Val Asp Leu Arg Tyr
        515                 520                 525

Gly Asn Gly Gly Leu Gly Gly Tyr Gly Asp Ile Pro Ala Asn Arg Ala
    530                 535                 540

Asp Val Asn Ile Ala Gly Phe Ile Gln Asp Leu Phe Gly Gln Pro Thr
545                 550                 555                 560

Ser Gly Leu Ala Ala Gln Ala Ser Thr Asn Asn Ala Gln Val Leu Ala
            565                 570                 575

Gln Val Arg Gln Phe Leu Asn Gln
            580

<210> SEQ ID NO 43
<211> LENGTH: 46
<212> TYPE: DNA
<213> ORGANISM: Artificial Sequence
<220> FEATURE:
<223> OTHER INFORMATION: forward primer

<400> SEQUENCE: 43
aaactaaaat ctaaaagatc tcaaggcaat ttttctcgcc aggaag         46

<210> SEQ ID NO 44
<211> LENGTH: 49
<212> TYPE: DNA
<213> ORGANISM: Artificial Sequence
<220> FEATURE:
<223> OTHER INFORMATION: reverse primer

<400> SEQUENCE: 44
ggtttcttta ccagactcga gttattgatt cagaaattga cggacctgt      49

<210> SEQ ID NO 45
<211> LENGTH: 30
<212> TYPE: DNA
<213> ORGANISM: Artificial Sequence
<220> FEATURE:
<223> OTHER INFORMATION: forward primer

<400> SEQUENCE: 45
tctggtaaag aaaccgctgc tgcgaaattt                           30

<210> SEQ ID NO 46
<211> LENGTH: 30
<212> TYPE: DNA
<213> ORGANISM: Artificial Sequence
<220> FEATURE:
<223> OTHER INFORMATION: reverse primer

<400> SEQUENCE: 46
tttagatttt agtttgtcac tatgatcaat                           30

<210> SEQ ID NO 47
<211> LENGTH: 30
<212> TYPE: DNA
<213> ORGANISM: Artificial Sequence
<220> FEATURE:
<223> OTHER INFORMATION: forward primer

```
<400> SEQUENCE: 47
cgtcgcacaa cgatggcagc aggcgttgac                                              30

<210> SEQ ID NO 48
<211> LENGTH: 30
<212> TYPE: DNA
<213> ORGANISM: Artificial Sequence
<220> FEATURE:
<223> OTHER INFORMATION: reverse primer

<400> SEQUENCE: 48
gctgatcgtg aacaggtagt acttgccgtc                                              30

<210> SEQ ID NO 49
<211> LENGTH: 29
<212> TYPE: DNA
<213> ORGANISM: Artificial Sequence
<220> FEATURE:
<223> OTHER INFORMATION: forward primer

<400> SEQUENCE: 49
cgtcgcacca cctttgcggc gggtgtgga                                               29

<210> SEQ ID NO 50
<211> LENGTH: 30
<212> TYPE: DNA
<213> ORGANISM: Artificial Sequence
<220> FEATURE:
<223> OTHER INFORMATION: reverse primer

<400> SEQUENCE: 50
gctgatcgtg aagatgtagt acttgccgtt                                              30
```